(12) United States Patent
Chang et al.

(10) Patent No.: US 8,551,695 B2
(45) Date of Patent: Oct. 8, 2013

(54) STARCH BINDING DOMAIN AND USE THEREOF

(75) Inventors: Margaret Dah-Tsyr Chang, Hsinchu (TW); Ping-Chiang Lyu, Hsinchu (TW); Yuh-Ju Sun, Hsinchu (TW); Chia-Chin Sheu, Taoyuan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 13/355,966

(22) Filed: Jan. 23, 2012

(65) Prior Publication Data

US 2012/0225492 A1 Sep. 6, 2012

Related U.S. Application Data

(63) Continuation-in-part of application No. 12/447,848, filed as application No. PCT/CN2006/002915 on Oct. 31, 2006, now abandoned.

(51) Int. Cl.
*C12Q 1/00* (2006.01)

(52) U.S. Cl.
USPC ............................................................ 435/4

(58) Field of Classification Search
None
See application file for complete search history.

(56) References Cited

U.S. PATENT DOCUMENTS

2006/0198792 A1* 9/2006 Chang et al. .................... 424/50

OTHER PUBLICATIONS

Xie et al (Biochemistry vol. 40, pp. 9167-9176, 2001).*

* cited by examiner

*Primary Examiner* — Labert Navarro
(74) *Attorney, Agent, or Firm* — WPAT, P.C.; Anthony King

(57) ABSTRACT

The present invention provides a method for identifying starch binding sites of starch binding domain in CBM family. The CBM family is consisting of CBM20, CBM21, CBM25, CBM26, CBM34, and CBM41. The method further comprises predicting starch binding sites of starch binding domain in CBM family using the identified starch binding sites of starch binding domain with same topology.

9 Claims, 21 Drawing Sheets

β1    β2    β5    β4

N-sheet

C-sheet

180°

Type I topology   Type II topology

US 8,551,695 B2

STARCH BINDING DOMAIN AND USE THEREOF

CROSS-REFERENCE TO RELATED APPLICATIONS

This application is a Continuation-in-part of the pending U.S. patent application Ser. No. 12/447,848 filed on Apr. 29, 2009, for which priority is claimed and is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a method for identifying starch binding sites of starch binding domain in CBM family.

DESCRIPTION OF PRIOR ART

Production of proteins by expression in microbial systems has become a significant source of high value, medically important proteins. Purification and recovery of recombinant proteins are major considerations in the design of a fermentation process. While traditional methods of protein purification can be used to isolate a product, improved methods include the use of recombinant proteins. Recombinant proteins can be purified by affinity column chromatography, the desired component of the recombinant protein being purified by virtue of its covalent attachment to a polypeptide, which binds to an affinity matrix.

Certain systems exist for isolating proteins by the principle of affinity column chromatography.

U.S. Pat. No. 5,643,758 describes a system comprising maltose-binding protein (MBP). A cloned gene is inserted into a pMAL vector down-stream from the malE gene, which encodes MBP. The vector is transformed to a host cell, then the recombinant protein can express in the host cell. The cell lysate or media fraction is loaded to a column containing affinity matrix amylose and washed several times, then using a large amount of maltose to elute the recombinant protein.

U.S. Pat. No. 5,202,247 describes a system comprising cellulose-binding domain. A cellulose column can be used to purify the recombinant protein that contains cellulose-binding domain. The cell lysate or media fraction is loaded to the column and washed. The interaction between cellulose-binding domain and cellulose appears to be driven by hydrophobic interaction at neutral pH. The general method for elution used low polarity solvents such as ethlylene glycol, prior to removal of the low polarity solvents by dialysis and filtration.

These current protein purification systems have some disadvantages. The purification processes are inconvenient and laborious. The columns used in purification are expensive. Limitations for protein purification of these systems include unable to isolate the recombinant protein in certain conditions such as EDTA-containing samples as well as the current protein tags being used are relatively large as compared to the target protein bigger than that of this invention.

D: Two molecules of β-cyclodextrin are docked into RoCBM21. E and F: Docking of cyclomaltohexaicosaose (v-amylose) to RoCBM21. E. Schematic view and F surface view of RoCBM21 docked with v-amylose. In E, the strands are in yellow and the v-amyloses are shown as ball-and-stick structures. In F proteins are in yellow and v-amyloses are in white.

Figure 12:
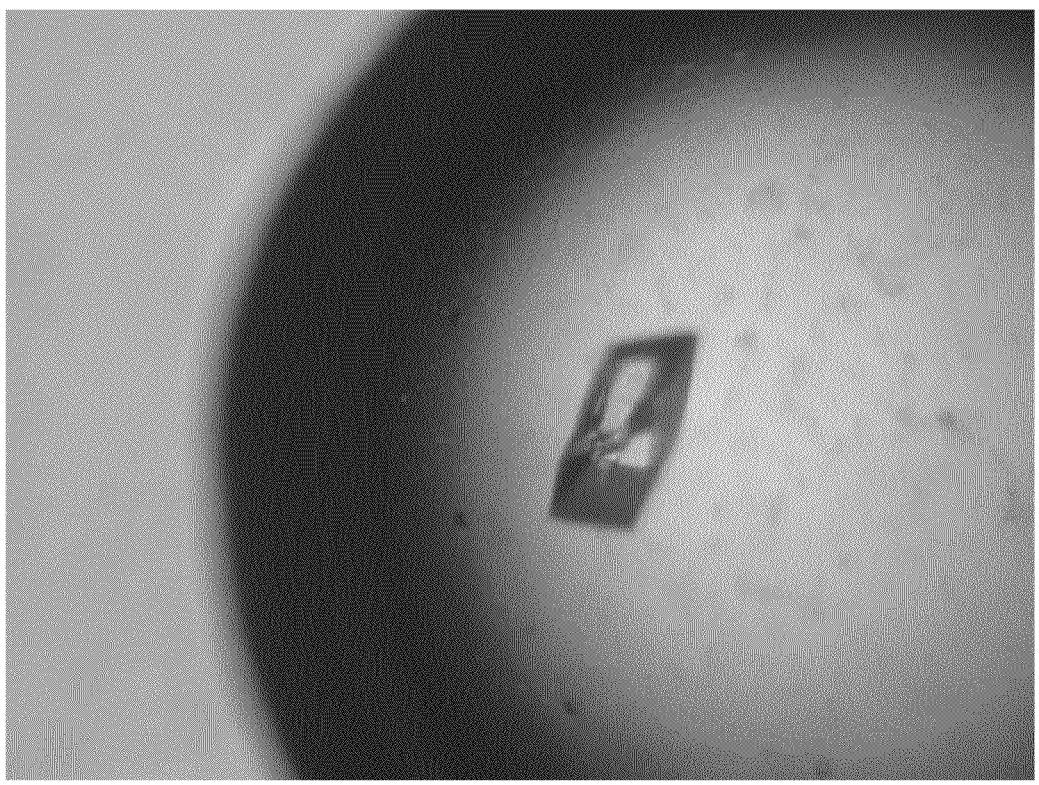

FIG. 12 shows the RoGACBM21-βCD complex crystals.

Figure 13:
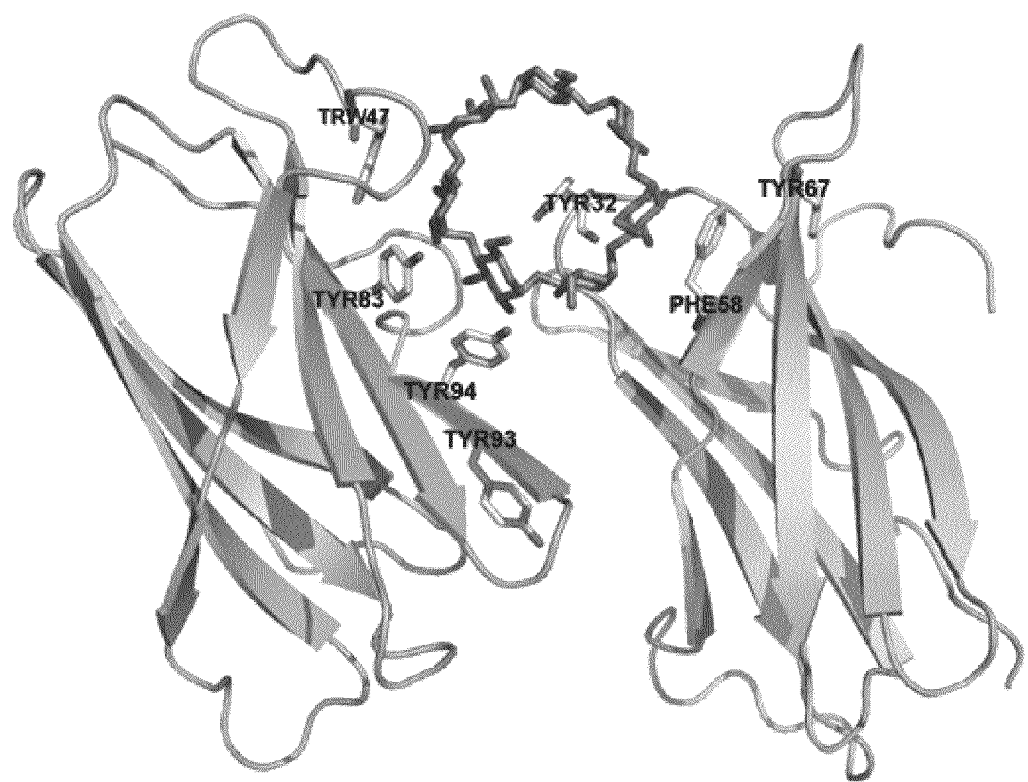

FIG. 13 shows the RoGACBM21-βCD complex.

SUMMARY OF THE INVENTION

The present invention provides a method for identifying starch binding sites of starch binding domain in CBM family, comprising: (a) obtaining structure of objective starch binding domain by NMR spectroscopy; (b) simulating binding mode of objective starch binding domain between affected residues from chemical shift perturbation of the structure of objective starch binding domain and an oligosaccharide via a docking tool to present predicted binding residues; (c) obtaining crystal structure of a complex of objective starch binding domain and the oligosaccharide via X-ray crystallography to present ligand-binding residues; and (d) selecting matched residues from the predicted binding residues and the ligand-binding residues to identify the starch binding sites of starch binding domain; the CBM family is consisting of CBM20, CBM21, CBM25, CBM26, CBM34, and CBM41. The method further comprises predicting starch binding sites of starch binding domain in CBM family using the identified starch binding sites of starch binding domain with same topology.

DETAILED DESCRIPTION OF THE INVENTION

The present invention provides a method for identifying starch binding sites of starch binding domain in CBM family, comprising: (a) obtaining structure of objective starch binding domain by NMR spectroscopy; (b) simulating binding mode of objective starch binding domain between affected residues from chemical shift perturbation of the structure of objective starch binding domain and an oligosaccharide via a docking tool to present predicted binding residues; (c) obtaining crystal structure of a complex of objective starch binding domain and the oligosaccharide via X-ray crystallography to present ligand-binding residues; and (d) selecting matched residues from the predicted binding residues and the ligand-binding residues to identify the starch binding sites of starch binding domain; the CBM family is consisting of CBM20, CBM21, CBM25, CBM26, CBM34, or CBM41. In a preferred embodiment, the CBM family is CBM20 or CBM21. In a preferred embodiment, the oligosaccharide is maltotriose, maltoheptaose, or β-cyclodextrin. In a preferred embodiment, the docking tool includes but not limited to AutoDock. In a more preferred embodiment, the CBM family is CBM21.

The starch binding sites of starch binding domain are aromatic amino acids. In a preferred embodiment, the starch binding sites of starch binding domain are tyrosine, tryptophan, or phenylalanine. The identified starch binding sites of starch binding domain in CBM21, from the present invention, are residues 32, 47, 58, 67, 83, 93, or 94 in SEQ ID NOs. 1, 2, and 3.

The starch binding domain in CBM family is categorized into type I topology and type II topology. The method of the present invention further comprising obtaining protein topology of objective starch binding domain before step (a). Furthermore, the method of the present invention further comprises predicting starch binding sites of starch binding domain in CBM family using the identified starch binding sites of starch binding domain with same topology. The CBM family is consisting of CBM20, CBM21, CBM25, CBM26, CBM34, or CBM41.

The present invention relates to a starch binding domain (SBD) which has an amino acid sequence shown in SEQ ID No. 1, 2 or 3,

```
SEQ ID No. 1:
ASIPSSASVQ LDSYNYDGST FSGKIYVKNI AYSKKVTVVY

ADGSDNWNNN GNIIAASFSG PISGSNYEYW TFSASVKGIK

EFYIKYEVSG KTYYDNNNSA NYQVSTS;

SEQ ID No. 2:
ASIPSSASVQ LDSYNYDGST FSGKIYVKNI AYSKKVTVIY

ADGSDNWNNN GNTIAASYSA PISGSNYEYW TFSASINGIK

EFYIKYEVSG KTYYDNNNSA NYQVSTS;
or

SEQ ID No. 3:
ASIPSSASVQ LDSYNYDGST FSGKIYVKNI AYSKKVTVIY

ANGSDNWNNN GNTIAASYSA PISGSNYEYW TFSASINGIK

EFYIKYEVSG KTYYDNNNSA NYQVSTS;
``` allelic variation and derivatives thereof having starch-binding ability, with SEQ ID No 1, 2, or 3 being part of this starch binding domain.

The SBD of the present invention is obtainable from family members of carbohydrate binding module (CBM) CBM20 or CBM21. In an embodiment, the SBD is obtainable from starch binding domain of glucoamylase from CBM21. In a preferred embodiment, the SBD is obtainable from Rhizopus spp. In a more preferred embodiment, the SBD is obtainable from starch binding domain of glucoamylase of Rhizopus spp.

The SBD of the present invention has ligand binding (or carbohydrate binding) sites on aromatic group of amino acid residues 32, 47, 58, 67, 83, 93 and 94 of the sequence for carbohydrate-binding, wherein the amino acid residues are tyrosine or/and tryptophan. In a preferred embodiment, the active sites are residue 32 tyrosine, residue 47 tryptophan, residue 58 tyrosine, residue 83 tyrosine, residue 93 tyrosine, and residue 94 tyrosine.

The present invention also relates to a recombinant protein having:

(SBD)$m$-Ln-X-L'$p$-(SBD)$q$

SBD represents a starch binding domain, L represents a linker, L' represents a linker, X represents a target protein or polypeptide, m is 0, 1, or 2, n is 0 or 1, p is 0 or 1, and q is 0, 1, or 2, wherein the m and q are not 0 simultaneously. The SBD is as described above.

In a preferred embodiment, the linker is RoLK: linker of Rhizopus oryzae GA, PH: six histidines, PK: eight lysines, PPT: a threonine plus four repeats of proline-threonine [T (PT)$_4$], or 58L: the region between the cutting sites of SpeI and NcoI on pET39b(+).

The present invention also relates to complex comprising:

(SBD)$m$—X-(SBD)$q$

SBD represents a starch binding domain, X represents a carbohydrate, m is 0, 1, or 2, and q is 0, 1, or 2, wherein the SBD uses separate unit to simultaneously bind the carbohydrate.

In a preferred embodiment, the entity X is carbohydrate which has α-1,4-glucose linkage or α-1,6-glucose linkage in the structure. In a more preferred embodiment, the carbohydrate is oligomeric or cyclic carbohydrate. The starch binding domain binds to the carbohydrate by ligand bind (carbohydrate binding) site or conformation. The starch binding domain has multiple units depending on the carbohydrate size.

This invention further relates to a method for separating a recombinant protein comprising a starch binding domain as described above comprising: (a) applying the biological liquid containing the recombinant protein directly to an affinity matrix; and (b) eluting the recombinant protein by temperature alteration, pH, ion strength, sugar concentration or enzyme component.

The affinity matrix of the method contains the formula:

$$(X—X)_n$$

X means glucose molecule, the linkage between glucose and glucose is α-1,4-linkage or α-1,6-linkage and n is 1 or more than 1; in any part structure thereof comprising main chain, side chain, or modified residue. In a preferred embodiment, the affinity matrix is starch. In a preferred embodiment, the temperature alteration is increasing the temperature to 37° C. or higher, and the step (a) is performed under 0-25° C.

EXAMPLE

The examples below are non-limiting and are merely representative of various aspects and features of the present invention.

Microbial Strains and Plasmids

*Escherichia coli* Top10F' (F' {proAB lacI$^q$, lacZΔM15, Tn10(Tet$^R$)} mcrA, Δ(mrr-hsdRMS-mcrBC), 80lacZΔM15, ΔlacX74, deoR, recA1, araD139, Δ(ara-leu)7697, galU, galK, rpsL (Str$^R$) endA1, nupG λ$^-$) was used as a host for vector construction and DNA manipulation.

*Escherichia coli* BL21-CodonPlus® (DE3) (Stratagene, USA) (B F$^-$ ompT hsdS($r_B^-$ $m_B^-$) dcm$^+$ Tet$^r$ galλ(DE3) endA Hte [argU proL Cam$^r$] [argU ileY leuW Strep/Spec$^r$]) was used as the host for the production of fusion protein.

The vector pET-23a(+) (Novagen, USA), containing a T7 promoter, was used to express the fusion protein in *E. coli* cells and for sequencing analysis.

Bacterial Culture

*E. coli* was grown in Luria-Bertani (LB) medium [1% (w/v) tryptone, 2% (w/v) yeast extract, 2% (w/v) sodium chloride, pH 7.5] containing 50 μg/ml ampicillin. The transformants were selected on solid plates consisting of the LB medium with 1.5% agar, and 50 μg/ml ampicillin at 37° C.

Example 1

(A) Construction of Plasmids

Figure 1:
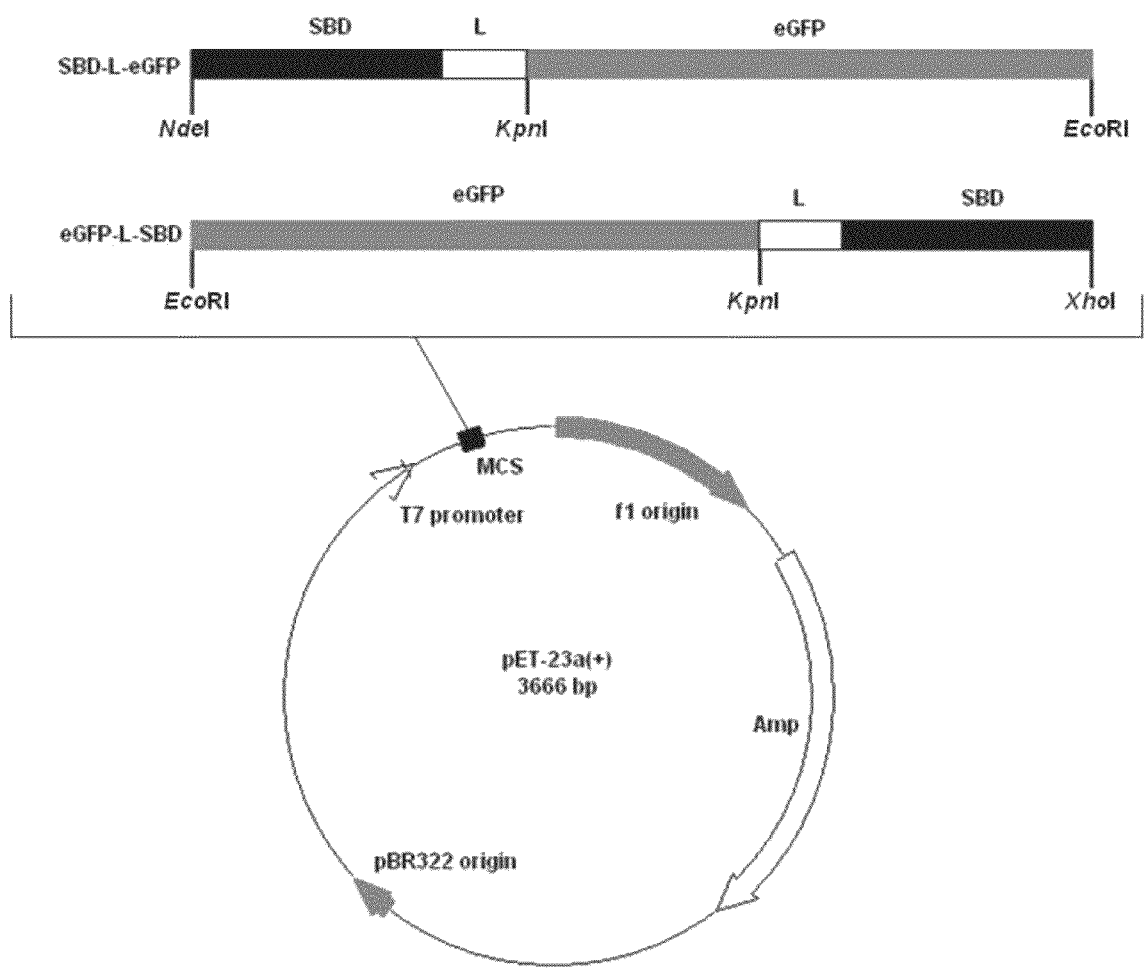
FIG. 1 shows the plasmid map for recombinant pET-23a (+)-SBD-L-eGFP and pET-23a(+)-eGFP-L-SBD.

The schematic representation of the recombinant constructs is shown in FIG. 1. The fragments of eGFP, linkers and SBD were amplified by PCR with the designed primers, and their sequences are shown in Table 1. The linker region is substituted with five linker candidates (RoLK: linker of *Rhizopus oryzae* GA, PH: six histidines, PK: eight lysines, PPT: a threonine plus four repeats of proline-threonine [T (PT)$_4$], and 58L: the region between the cutting sites of SpeI and NcoI on pET39b(+)). The PCR reactions were prepared as follows: 10 ng template, 0.5 μl of each primer (10 μM), 5 μl reaction buffer (10×), 5 μl deoxynucleotides (2.5 mM), 0.8 μl Ex Taq DNA polymerase (Takara Mirus Bio, Japan, 5 U/μl) in a final volume of 50 μl with ddH$_2$O. This mixture was subjected to 1 cycle of 95° C. for 5 min and 30 cycles of 95° C. for 30 sec (Denaturation), 53° C. for 30 sec (Annealing), 72° C. for 20 sec to 2 min (Extension) and 1 cycle of 72° C. for 5 min.

TABLE 1

| Synthetic oligonucleotide primers | |
|---|---|
| Primer names | Sequences of synthetic oligonucleotides |
| LK-F-HindIII | 5'-TCCC<u>AAGCTT</u>TCCAAGCCCACTACTACT |
| LK-R-KpnI | 5'-ACG<u>GGGTACC</u>GTTACCAGTTGGGAATGA |
| 58L-F-HindIII | 5'-CCC<u>AAGCTT</u>ACTAGTGGTTCTGGTCATCAC |
| 58L-R-NdeI | 5'-AA<u>CATATG</u>CATGGTTGAGGAGAAGCCCG |
| SBD-F-KpnI | 5'-TTCG<u>GGGTACC</u>GCAAGTATTCCTAGCA |
| SBD-F-NdeI | 5'-GGGAATTC<u>CATATG</u>GCAAGTATTCCTA |
| SBD-R-XhoI | 5'-TCCG<u>CTCGAG</u>TCATGTAGATACTTGG |
| PK-F-HindIII | 5'-TGCGCCC<u>AAGCTT</u>AAGAAGAAGAAGAAGAAGAAGGC AAGTATTCCTAGCAGTGCTTC |
| PK-R-KpnI | 5'-CCG<u>GGGTACC</u>CTTCTTCTTCTTCTTCTTCTTCTTTCTAGA TACTTGGTAATTGGC |
| PH-F-HindIII | 5'-TCCC<u>AAGCTT</u>CACCACCACCACCACCACGCAAGTATTCCTA GCAGTGCTT |
| PH-R-KpnI | 5'-ACG<u>GGGTACC</u>GTGGTGGTGGTGGTGGTGTAGATACTTGG TAATTGGC |
| PPT-F-HindIII | 5'-TCCC<u>AAGCTT</u>ACTCCGACTCCGACTCCGACTCCGACTGCAA GTATTCCTAGCAGTGCTTC |
| PPT-R-KpnI | 5'-TCG<u>GGGTACC</u>AGTCGGAGTCGGAGTCGGAGTCGGAGTTGTA GATACTTGGTAATTGGC |

TABLE 1-continued

Synthetic oligonucleotide primers

| Primer names | Sequences of synthetic oligonucleotides |
|---|---|
| SBD-F-NdeI | 5'-GGGAATTC<u>CATATG</u>GCAAGTATTCCTA |
| mFT-F-KpnI | 5'-TTTCGG<u>GGTACC</u>CAG AGTGAGCCGGAG |
| GFP-F-EcoRI | 5'-G<u>GAATTC</u>ATGGTGAGCAAGGGC |
| GFP-F-KpnI | 5'-TATCGG<u>GGTACC</u>ATGGTGAGCAAGGGCGAGGAGCTGTT |
| GFP-R-HindIII | 5'-CCC<u>AAGCTT</u>CTTGTACAGCTCGTC |

The sites for restriction enzymes are underlined.

The fragments from the previous step were ligated with pGEM®-T Easy vector (Promega, USA). One hundred ng insert DNA fragment, 1 µl vector, 1 µl ligase buffer [66 mM Tris-HCl (pH 7.6), 6.6 mM $MgCl_2$, 10 mM DTT and 0.1 mM ATP] and 1 µl T4 ligase (Takara Mirus Bio, Japan) solution, with addition of dd$H_2O$ that made the final volume as 10 µl, were mixed together and placed at 16° C. for 16 hr. The ligation product was then transformed into competent E. coli cells. Transformants of E. coli harboring the T-vector with the desired sequences were selected from the blue-white selection plates. The plasmids were purified by Gene-Spin™ Miniprep Purification Kit (Protech, Taiwan) from the further cell culture of the selected colonies. The plasmids underwent the digestion by specific restriction enzymes, and then the digested fragments were separated by electrophoresis, which was carried out with 1% agarose gel in 1×TAE buffer (40 mM Tris Base, 40 mM acetic acid, and 1 mM EDTA) at a voltage of 100 V to size the DNA fragments. EtBr (ethidium bromide, 0.5 mg/ml) solution was used to stain the gel for 10 min, and the DNA fragments were shown under UV light. The desired fragments were purified by the Gel/PCR DNA fragment extraction kit (Geneaid Biotech, Taiwan) for further usage.

Before ligation, pET-23a(+) vector was treated with specific restriction enzymes. For the constructs containing the SBD at the 5' end, the vector was treated with NdeI and EcoRI, and the DNA fragment of SBD with the linker was digested by NdeI and KpnI. The eGFP DNA fragment was cut by KpnI and EcoRI. On the other hand, for constructing the plasmid with the SBD at the 3' end, the vector was digested by EcoRI and XhoI, while the DNA fragment of eGFP with the linker was treated with EcoRI and HindIII, and the SBD with the linker was cut by HindIII and XhoI. The ligation product was transformed into competent E. coli Top10F' cells as for the DNA preparation and confirmation of DNA sequence prior to the transformation of E. coli BL21-CodonPlus® (DE3).

(B) Preparation of Competent Cells and Transformation of E. Coli

The $CaCl_2$-mediated transformation technique developed by Mandel and Higa in 1970 was applied to prepare competent E. coli Top10F' and BL21-CodonPlus® (DE3) cells prior to transformation. To begin with, a 100 µl aliquot of frozen E. coli cells was inoculated with 5 ml LB medium including 50 µg/ml tetracycline and grown at 37° C. for 16 hr, and then a 100 µl aliquot of the overnight cells was incubated in 5 ml fresh LB medium with tetracycline at 37° C. until the value of $OD_{600}$ reached 0.5~0.6. The cell pellet was collected by centrifugation at 16,000×g for 5 min at 4° C. and resuspended in 10 ml ice-cold calcium chloride (100 mM). The incubation of the cells was carried out in an ice-water bath for 30 min before the centrifugation. The final competent cell suspension was obtained by gently resuspending the cell pellet from the previous step in 500 µl ice-cold calcium chloride containing 15% glycerol for 3 hr.

In transformation of E. coli, 100 µl aliquot of the well-prepared competent cells was mixed with 10 µl ligation mixture and incubated on ice for 30 min. After the heat shock step, where the mixture was placed at 42° C. for 90 sec, 500 µl LB medium was added to the mixture for further 30-min incubation at 37° C. Finally, the cells were collected by centrifugation at 16,000×g for 10 min at 25° C. and plated on LB agar plates containing 50 µg/ml ampicillin. The plates were incubated at 37° C. for 16 hr.

(C) Mini-Preparation of Plasmid

Recombinant E. coli was cultured in LB medium at 37° C. for 16 hr and harvested by centrifugation at 16,000×g for 5 min at 4° C. Plasmid DNA was isolated by Gene-Spin™ Miniprep Purification Kit. The pellet was resuspended in 200 µl of solution I (50 mM EDTA, 25 mM Tris pH 8.0, 50 mM glucose). Two hundred microliters of solution II (0.2N NaOH, 1% SDS) was subsequently added and the microcentrifuge tube was inverted gently until the solution became clear. Two hundred µl of solution III (KOAc, 11.5% glacial acetic acid, pH 4.8) was added and the tube was inverted 5 to 6 times. The insoluble material was removed by centrifugation at 16,000×g for 5 min at 4° C. The supernatant was directly transferred to a spin column, and it was removed by centrifugation for 30 sec at 16,000×g. The filtrate was discarded, and 700 µl washing solution (70% ethanol) was added prior to the centrifugation for 1 min at 16,000×g. The filtrate was discarded and centrifuged at 16,000×g for another 3 min at 4° C. to remove residual ethanol. The spin column was removed and placed in a new eppendorf tube. Fifty to 100 µl of sterilized dd$H_2O$ was added into the column Finally the DNA was eluted by centrifuge at 16,000×g for 5 min at 4° C. and stored at −20° C.

(D) In Situ PCR

Several colonies on the plates of E. coli transformant were selected and used as PCR templates. The transformant colony as the remplate, 0.3 µl of 10 µM forward primer, 0.3 µl of 10 µM reverse primer, 2 µl of 2.5 mM dNTP (dGTP, dATP, dCTP and dTTP), 2 µl of 10× reaction buffer, 0.3 µl of 5 U/µl Vio Taq DNA polymerase (Viogene, USA) and 15.1 µl dd$H_2O$ were mixed together. The Perkin Elmer Gene Amp PCR system 2400 was utilized. The condition of the thermal cycles is as follows:

| Stage | Temperature | Time | Number of Cycles |
|---|---|---|---|
| 1 | 95° C. | 5 min | 1 |
| 2 | 95° C. | 30 sec | 30 |
|   | 53° C. | 30 sec |   |
|   | 72° C. | 30 sec~1 min 30 sec |   |
| 3 | 72° C. | 7 min | 1 |

(E) DNA Sequencing

The sequencing reactions were performed by BigDye® Terminator V3.1 Cycle Sequencing Kit (ABI, USA). The reaction mixtures were subjected to 1 cycle of 96° C. for 1 min, 25 cycles of 96° C. for 30 sec, 50° C. for 30 sec and 60° C. for 2 min. The products were then mixed with 2 µl 3M sodium acetate, pH 4.6, 50 µl 95% ethanol, and 10 µl ddH$_2$O and placed at 25° C. for 15 min to precipitate the extension products. They were centrifuged at 16,000×g for 20 min at 4° C., and the supernatants were removed. Hundred and eighty µl of 70% ethanol was added to each tube with brief mixing. They were spun at 16,000×g for 5 min at 4° C., and the supernatants were discarded completely. The tubes containing the extended DNA products were dried in a vacuum centrifuge for 5 min and then 10 µl Hi-Di formamide was added to dissolve the products for autosequencing. Automated DNA sequencing was performed by ABI PRISM® 3100 Genetic Analyzer.

(F) Expression of Fusion Protein by *E. Coli*

*E. coli* BL21-CodonPlus® (DE3) was used as the bacterial host to produce fusion proteins. The plasmid containing the gene fragment of fusion protein was transformed into competent *E. coli* BL21-CodonPlus® (DE3) cells, which were selected by LB agar plates containing 50 µg/ml ampicillin with growing at 37° C. for 16 hr. A single colony was inoculated into 1 ml LB containing 50 µg/ml ampicillin for the incubation at 37° C., until the OD$_{600}$ reached 0.4 to 0.6. Induction was performed at 20° C., as isopropyl-β-D-thiogalactopyranoside (IPTG) was added to a final concentration of 1 mM. After 16 hr, the cells were harvested and resuspended in 0.1 ml binding buffer (50 mM NaOAc, pH 5.5) and lyzed by sonicator (Misonix, USA). The soluble and insoluble forms of the fusion proteins were separated by centrifugation at 16,000×g at 4° C. for 10 min.

(G) Sodium Dodecyl Sulphate-Polyacrylamide Gel Electrophoresis (SDS-PAGE)

SDS-discontinuous PAGE was performed based on the method of Laemmli [25], in which 1 mm slab gel composing of resolving gel (pH 8.8) and stacking gel (pH 6.8) was used. Samples were treated with sample buffer [100 mM Tris-HCl (pH 6.8), 200 mM DTT, 4% SDS, 0.2% bromophenol blue, and 20% glycerol] at 99° C. for 10 min. Electrophoresis was carried out on 12% (w/v) polyacrylamide gel at 25 mA for 60 min by the Electrical Supply MP-250.

Coomassie Blue solution (2.5% Coomassie brilliant blue R-250, 45% methanol, and 10% acetic acid) was used to stain the gel after electrophoresis for 15 min The gel was placed in destain I buffer (40% methanol and 10% acetic acid) for 1 hr as the de-staining step, and then it was put in destain II buffer (7% methanol and 5% acetic acid) for further destaining to remove the remaining stain. The protein molecular weight marker (Fermentas, USA) was loaded in parallel.

(H) Determination of Protein Concentration

Protein concentration of the samples were determined by the method of bicinchoninic acid assay (BCA Assay Kit, Pierce, USA), with bovine serum albumin (BSA) as the standard.

(I) Preparation of Purified Fusion Proteins by Amylose Resin Chromatography

The amylose resin was poured in a 2.5×10 cm column. The cell pellets of *E. coli* containing the fusion protein was resuspended in binding buffer (50 mM NaOAc, pH 5.5), and then sonicated. After centrifugating them at 16,000×g for 15 min at 4° C., the clear supernatant was retained for chromatography. After the column was washed with 8 column volumes of binding buffer, the clear cell lysate was loaded to the column at a flow rate of 1 ml/min. The fusion protein was then eluted by elution buffer (10 mM glycine/NaOH, pH 11.0) after the column was washed with another 12 column volumes of the binding buffer.

(J) Result

Figure 2:
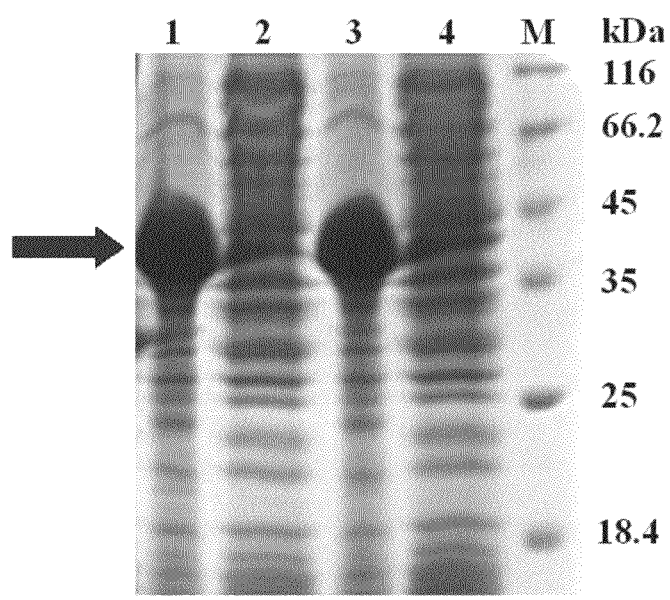
FIG. 2 shows SDS-PAGE analysis of SBD-PK-eGFP and SBD-PPT-eGFP expressed by E. coli.
Figure 3:
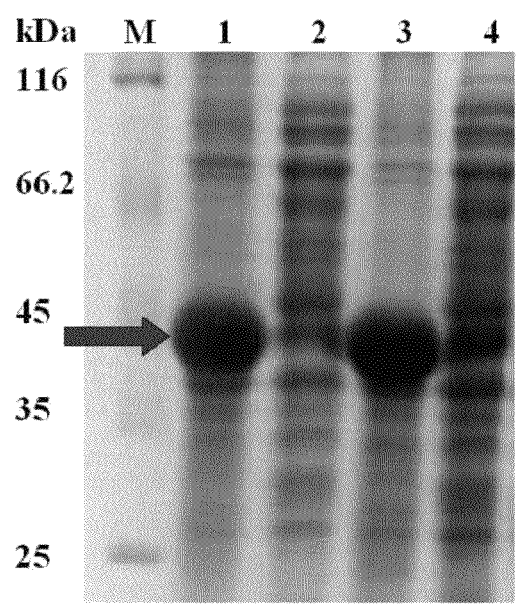
FIG. 3 shows SDS-PAGE analysis of eGFP-PK-SBD and eGFP-PPT-SBD expressed by E. coli.

In order to expand the application potentiality of using SBD as an affinity tag and investigate the effect of various peptide linkers on protein expression and purification, several recombinant clones containing eGFP and SBD with different linkers, 58L, RoLK, PH, PK and PPT, were constructed as illustrated in FIG. 1. Among the ten fusion proteins, five fusion proteins possessed an SBD at their N-termini, whereas the others contained a C-terminal SBD. In the case of having an N-terminal SBD, overexpression of soluble SBD-58L-eGFP, SBD-RoLK-eGFP, and SBD-PH-eGFP was achieved in *E. coli* expression system, while SBD-PK-eGFP and SBD-PPT-eGFP were expressed as inclusion bodies. When SBD was located at the C-terminus, eGFP-58L-SBD, eGFP-RoLK-SBD and eGFP—PH-SBD were also overexpressed in soluble fractions, but the expression of eGFP-PK-SBD and eGFP—PPT-SBD led to generation of inclusion bodies as well. Overexpression of the insoluble SBD-PK-eGFP and SBD-PPT-eGFP as well as that of eGFP-PK-SBD and eGFP-PPT-SBD is shown in FIG. 2 and FIG. 3, respectively. The molecular weight of the overexpressed SBD-PK-eGFP, SBD-PPT-eGFP, eGFP-PK-SBD and eGFP-PPT-SBD was estimated to be about 40 kDa as determined by 12% SDS-PAGE.

Figure 4:
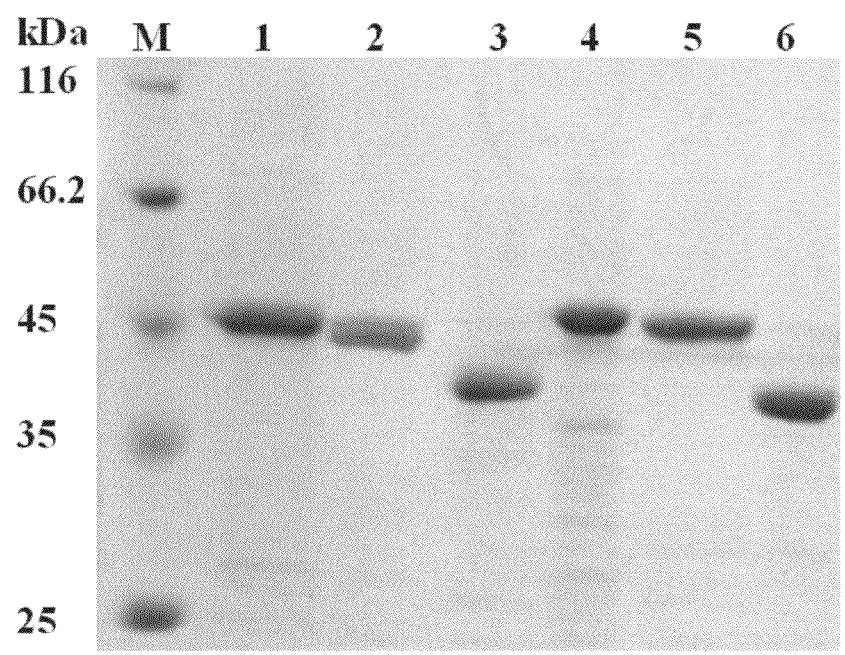
FIG. 4 shows SDS-PAGE analysis of purified fusion proteins.

The six fusion proteins (SBD-58L-eGFP, SBD-RoLK-eGFP, SBD-PH-eGFP, eGFP-58L-SBD, eGFP-RoLK-SBD and eGFP—PH-SBD) were successfully expressed by *E. coli* BL21-CodonPlus® (DE3), where the induction was performed at 20° C. for 16 hr in order to obtain soluble fusion proteins. After the cells were collected by centrifugation, resuspended in binding buffer (50 mM NaOAc, pH 5.5) and then sonicated, the supernatant with the soluble overexpressed fusion proteins was collected by centrifugation and subjected to affinity column chromatography using a column packed with amylose resin. Elution buffer (10 mM glycine/NaOH, pH 11.0) was applied to elute the pure fusion protein from the column The purified recombinant proteins were then analyzed by 12% SDS-PAGE as shown in FIG. 4. Approximately 100 to 150 mg of purified fusion protein could be obtained for all recombinant clones from 1 L cell culture. These proteins were used for the following characterization assays.

Example 2

(A) Effect of pH on Binding Ability

In the experiment of investigating the pH effects on binding ability, purified fusion proteins with a concentration of 16 µM were stirred in a buffer with various pH values and a final concentration of corn starch (Sigma-Aldrich, EC 232-679-6, USA) as 0.1 mg/ml at 25° C. for 1 hr. The binding was carried out at a pH value, ranging from 2.0 to 11.0, where the buffers included 100 mM glycine/HCl (pH 2-3), 100 mM sodium acetate/acetic acid (pH 4-5), 100 mM $Na_2HPO_4/NaH_2PO_4$ (pH 6-7), 100 mM Tris/HCl (pH 8) and 100 mM glycine/NaOH (pH 9-11). The free fusion protein concentration in the supernatant before and after the binding was determined by BCA assay. The relative binding ability of the fusion protein assayed at pH 5.0 was normalized as 100%.

(B) Effect of Temperature on Binding Ability

In the investigation of temperature effects on starch binding ability, purified fusion proteins at a concentration of 16 µM were stirred in binding buffer (50 mM NaOAc, pH 5.5) with a final concentration of corn starch as 0.1 mg/ml at 4° C., 25° C. and 37° C. for 3 hr. The free fusion protein concentration in the supernatant before and after the binding was determined by BCA assay. The relative binding ability of the fusion protein assayed at 4° C. was normalized as 100%.

(C) Purification by Stirring Method

This purification method was referred to a stirring method developed for purifying *Pseudomonas amyloderamosa* isoamylase (Fang, T. Y. et al., (1994) *Enzy Microb Tech* 16, 247-252). Cell pellets of *E. coli* containing the fusion protein were resuspended in binding buffer (50 mM NaOAc, pH 5.5), and then sonicated. After centrifugation at 16,000×g for 15 min at 4° C., the insoluble pellet was discarded. Fifty mg of corn starch (Sigma, EC 232-679-6) was washed with 1 ml of elution buffer (10 mM glycine/NaOH, pH 11.0) for 3 times, and then washed with 1 ml of $ddH_2O$. The $ddH_2O$ was removed by centrifugation at 16,000×g for 5 min. One ml of the supernatant containing the fusion protein was incubated with 50 mg starch from the starch solution at 25° C. with continuous stirring for 3 hr. The supernatant was removed after centrifugation at 16,000×g for 10 min at 4° C. The starch pellet was washed with 1 ml of binding buffer for 3 times, and then eluted by 250 µl of elution buffer for 4 times. The fractions from washing and elution were all retained for SDS-PAGE and further analysis.

(D) Purification by Starch Column Chromatography

This purification method was referred to a purification scheme developed for purifying *Pseudomonas amyloderamosa* isoamylase by funnel-type glass filter with raw starch (Lin, L. L. et al., (1994) *Lett Appl Microbiol* 19, 383-385). The cell pellets of *E. coli* containing the fusion protein were resuspended in binding buffer (50 mM NaOAc, pH 5.5), and then sonicated. After centrifugation at 16,000×g for 15 min at 4° C., the insoluble pellet was discarded. Two hundred mg of corn starch (Sigma) was washed with 2 ml of elution buffer (10 mM glycine/NaOH, pH 11.0) for 3 times, and then washed with 2 ml of $ddH_2O$. The starch pellet was washed with 2 ml binding buffer (50 mM NaOAc, pH 5.5) for 3 times, and finally dispersed in binding buffer. The starch solution was packed in a 5-ml disposable syringe, in which the needle was removed and filter paper was placed at the bottom to stop the starch from flowing away. Three ml of soluble fraction collected after sonication of the cells was loaded on the starch column, and the flowing was achieved by gravity. Unspecific bound proteins were washed with 6 ml of binding buffer, and then 3 ml of elution buffer was used to elute the fusion protein. The washing and elution steps could be speeded up by suction using another syringe at the bottom. The fractions from washing with binding buffer and eluting with elution buffer were all retained for SDS-PAGE and further analysis.

(E) Purification by Modified Starch Column Chromatography

Figure 5:
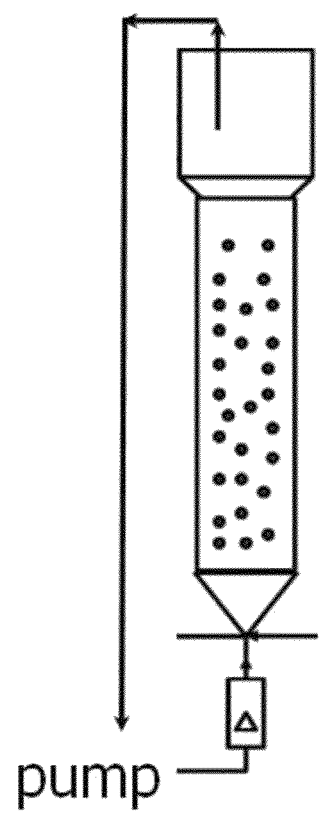
FIG. 5 shows purification of SBD-PH-eGFP using modified starch column chromatography.

The modification in starch column chromatography was achieved by combining it with fluidized bed adsorption (Hicketier, M. and Buchholz, K. (2002) *J Biotechnol* 93, 253-268; Roy, I. et al., (2000) *Protein Expr Purif* 20, 162-168). The cell pellets of *E. coli* containing the fusion protein was resuspended in binding buffer (50 mM NaOAc, pH 5.5), and then sonicated. After centrifugation at 16,000×g for 15 min at 4° C., the insoluble pellet was discarded. Six hundred mg of corn starch (Sigma) was washed with 3 ml of elution buffer (10 mM glycine/NaOH, pH 11.0) for 3 times, and then washed with 3 ml of $ddH_2O$. The starch pellet was washed with 3 ml binding buffer (50 mM NaOAc, pH 5.5) for 3 times, and finally dispersed in binding buffer. The starch solution was packed in a 5-ml disposable syringe, in which the needle was removed and filter paper was placed at the bottom to stop the starch from flowing away. The set-up of the modified starch column is schematically presented in FIG. 5. The soluble fraction collected from the cells after sonication was forced into the bottom of starch column by peristaltic pump P1 (Amersham Pharmacia Biotech, USA), at a flowing speed as 1 ml/min. Unspecific bound proteins were washed with 6 ml of binding buffer, and then elution buffer was used to elute the fusion protein. The fractions from washing with binding buffer and eluting with elution buffer were all retained for SDS-PAGE and further analysis.

(F) Result

Effects of pH and Temperature on Adsorption to Raw Starch

Figure 6:
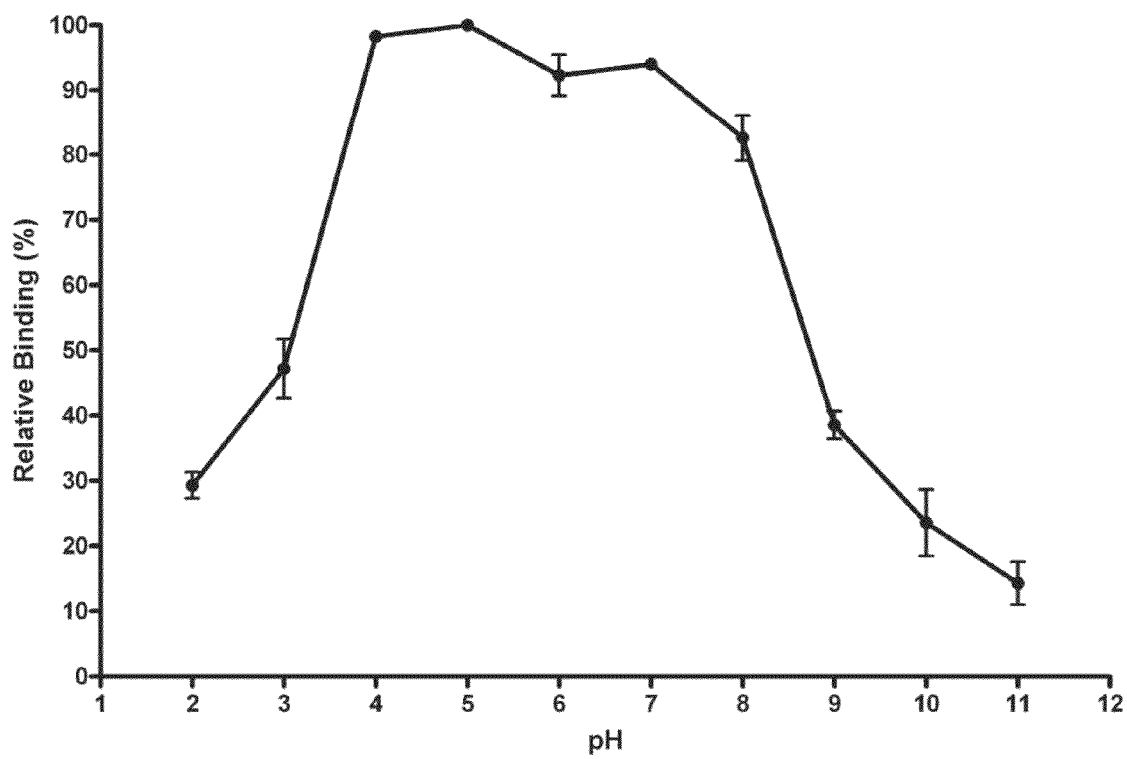
FIG. 6 shows effect of pH on binding ability of SBD-PH-eGFP to corn starch.

It has been revealed that SBD alone binds well to raw starch at pH 5.0 to 6.0, where the binding can be disrupted at a pH value above 6.0 or below 5.0, thus one of the fusion proteins, SBD-PH-eGFP, was selected for undergoing the binding assays at different pH values, ranging from 2.0 to 11.0 at 25° C., in order to confirm that the fusion protein containing SBD still retained the binding property at different pH. As shown in FIG. 6, the maximal binding of SBD-PH-eGFP onto corn starch occurred at pH 4.0 and pH 5.0, whereas the weakest binding was observed at pH 11.0. The relative binding was calculated as it was assumed that the binding at pH 5.0 was 100%. The fusion proteins bound to raw starch fairly well from pH 4.0 to pH 8.0, while the binding dropped quickly at the pH value lower than 4 or higher than 8.

Figure 7A:
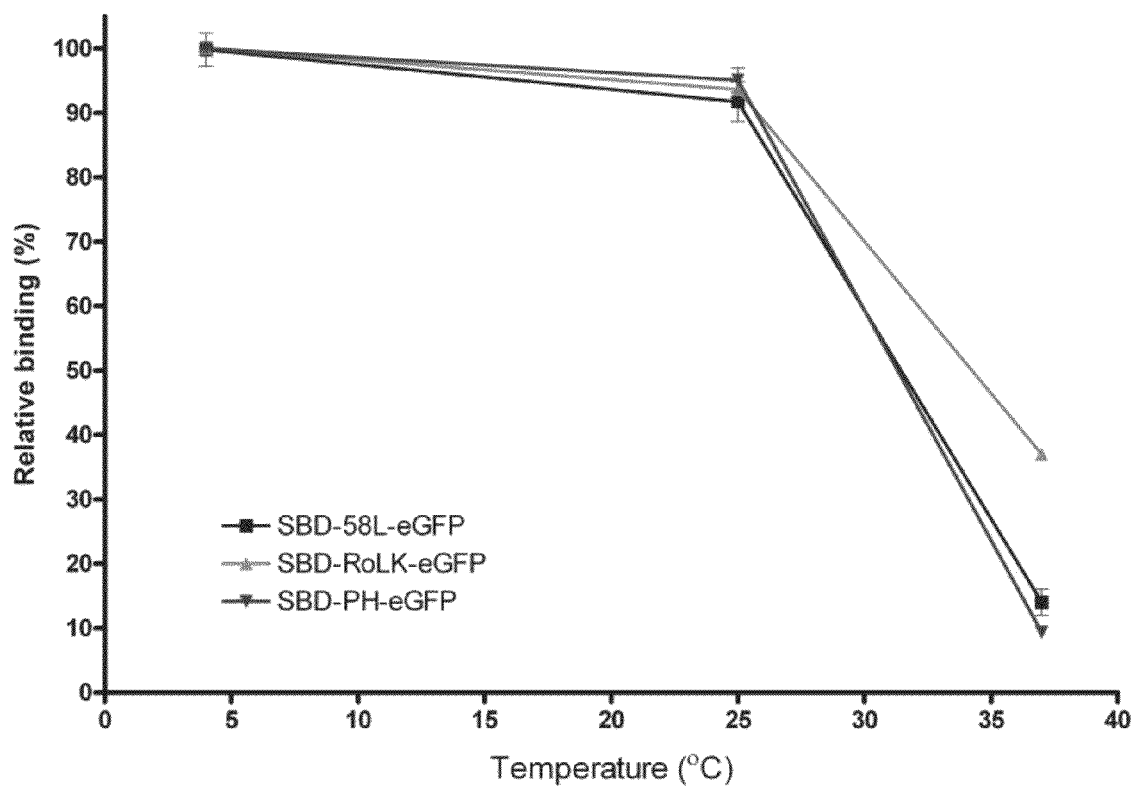
FIG. 7 shows effect of temperature on binding ability of fusion proteins to corn starch. (A) SBD in N-terminus of the recombinant protein. (B) SBD in C-terminus of the recombinant protein.
Figure 7B:
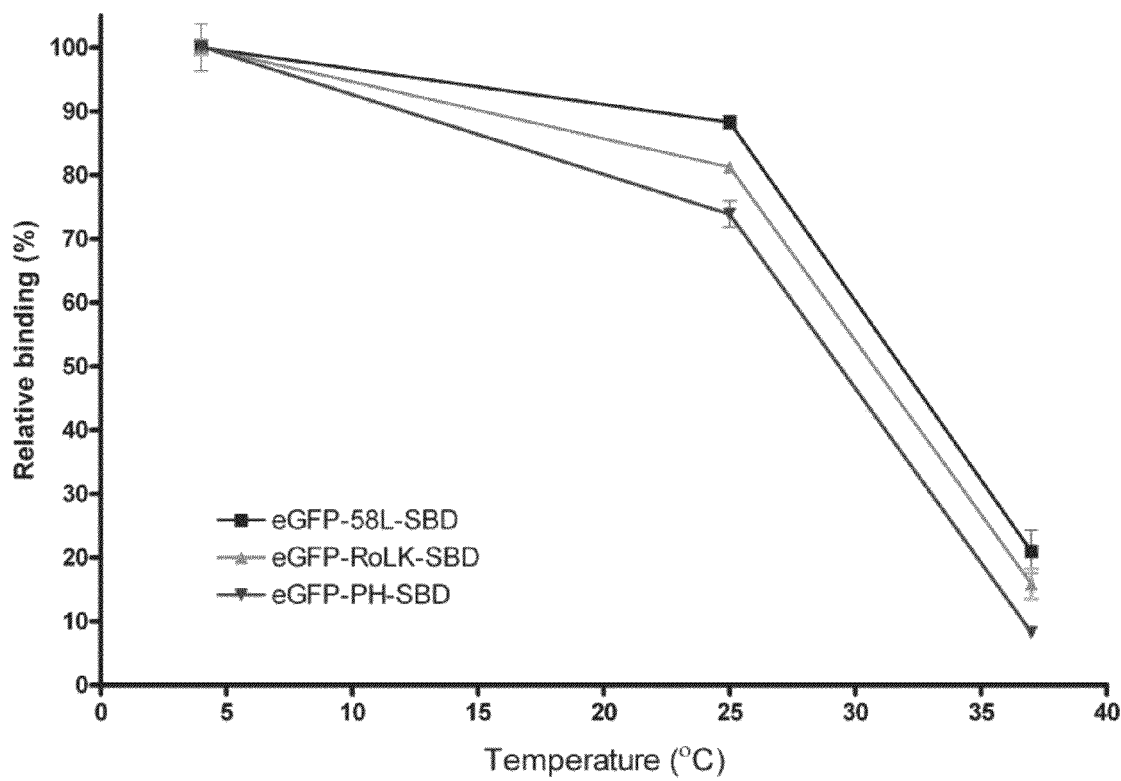

In addition, the binding assays of each purified fusion protein were carried out in binding buffer (50 mM NaOAc, pH 5.5) at different temperatures, and the result is shown in FIG. 7. The highest adsorption to corn starch occurred at 4° C. The relative binding at 25° C. decreased to 92%, 94%, 95%, 88%, 81% and 74% for SBD-58L-eGFP, SBD-RoLK-eGFP, and SBD-PH-eGFP, eGFP-58L-SBD, eGFP-RoLK-SBD and eGFP-PH-SBD, respectively. The binding was further disrupted when the binding was carried out at 37° C. The relative binding at 37° C. was reduced to 14%, 37%, 9%, 21%, 16% and 8% for SBD-58L-eGFP, SBD-RoLK-eGFP, and SBD-PH-eGFP, eGFP-58L-SBD, eGFP-RoLK-SBD and eGFP-PH-SBD, respectively. Consequently, the binding condition at a temperature range between 4° C. and 25° C. was required to achieve the high binding between corn starch and the fusion protein, while at less cost required in the cooling for experimental system, thus 25° C. was used for further experiments.

Example 3

(A) NMR Spectroscopy for Structure Determination

NMR data were acquired on a Bruker Avance 600 MHz or 800 MHz spectrometer. For structure determination, 1 mM RoCBM21 (either unlabeled, $^{15}$N-labeled, or $^{13}$C, $^{15}$N-double labeled) was dissolved in 10 mM sodium acetate, pH 4.5, and subjected to NMR experiments at 25° C. The protein concentrations were quantitated by Bio-Rad Protein Assay. Backbone assignment was accomplished with I-INCA, HN(CO)CA, HNCACB, CBCA(CO)NH, HNCO, and HN(CA)CO experiments (Cavanagh, J. et al., (1996) *Protein NMR spectroscopy*, Academic Press Inc.). Because RoCBM21 contains a relatively high proportion of aromatic residues, the assignment of aromatic side chains was assisted by HBCBCGCDHD and HBCBCGCDCEHE experiments (Yamazaki, T. et al., (1993) *J. Am. Chem. Soc.* 115, 11054-11055). The assignments of remaining atoms were accomplished using both homonuclear two-dimensional nuclear Overhauser enhancement spectroscopy (NOESY) and $^{15}$N heteronuclear single-quantum coherence-NOESY (HSQC-NOESY) with the assistance of through-bond correlation spectra. Homonuclear double quantum-filtered correlated spectroscopy (DQF-COSY), homonuclear total correlation spectroscopy (TOCSY) and $^{15}$N HSQC-TOCSY were utilized to obtain through-bond correlations. The mixing times were as follows: TOCSY spectra, 90 ms, and NOESY spectra, 50, 100 or 150 ms. All two-dimensional (2D) spectra were recorded with 512 t1 increments, and 2048 t2 complex data points were processed using TopSpin 1.3 (Bruker). Distance restraints were derived from NOESY spectra recorded with a 100-ms mixing time. A 2D $^{15}$N HSQC spectrum was recorded after dissolving the lyophilized RoCBM21 in 99% D$_2$O at 25° C. for 36 h to identify the protected amide protons. RoCBM21 did not readily dissolved after lyophilization, and therefore excess D$_2$O was added to completely dissolve the protein. The excess D$_2$O was subsequently removed by lyophilization to yield a 500-μl sample. Hydrogen bond constraints were obtained from the HSQC amide proton protection and confirmed with surrounding NOE signals and HNCOHB (through-hydrogen bond coherence)(Cordier, F., and Grzesiek, S. (1999) *J. Am. Chem. Soc.* 121, 1601-1602). Dihedral angle constraints were obtained using the TALOS program (Cornilescu, G et al., (1999) *J Biomol NMR* 13, 289-302) with chemical shifts of N, HA, CA, CB, C atoms. Sodium 2,2-dimethyl-2-silapentane-5-sulphonate (DSS) was used as an internal reference for proton chemical shifts, and heteronuclear chemical shifts were referenced assuming $\gamma^{15}$N/$\gamma^{1}$H=0.101329118 and $\gamma^{13}$C/$\gamma^{1}$H=0.251449530. The chemical shifts of RoCBM21 were deposited into the Biological Magnetic Resonance Data Bank (BMRB) under the entry number BMRB7083.

(B) Structure Calculation and Structural Analyses

Partially assigned peak lists and chemical shift lists were acquired from manual assignment using the program SPARKY (Goddard, T. D., and Kneller, D. G. (1999)). The peak intensities were derived using the default peak fitting protocol assuming Lorentzian line shapes. Structure calculations for RoCBM21 were carried out using CNS1.1 (Brunger, A. T. et al., (1998) *Acta Cryst.* D54, 905-921) and ARIA 2.0 (Nilges, M. et al., (1997) *J. Mol. Biol.* 269, 408-422) with torsion angle dynamics (TAD) and standard simulated annealing protocols (Nilges, M. et al., (1988) *FEBS Lett* 239, 129-136). These calculations were followed by explicit water refinement using the OPLS force field (Linge, J. P. et al., (2003) *Proteins* 50, 496-506). Of 200 structures we obtained, the 15 structures with the lowest total energies were selected for analysis. Their quality was assessed with PROCHECK-nmr (Laskowski, R. A. et al., (1993) *J. Appl. Cryst.* 26, 283-291). The atomic coordinates of the ensemble of structures were deposited into the Protein Data Bank (PDB) under the accession ID 2DJM.

(C) Chemical Shift Perturbations

To investigate the ligand-binding residues and ligand-binding interactions of RoCBM21, maltotriose, maltoheptaose, and β-cyclodextrin are applied to the chemical shift perturbation. Maltotriose and maltoheptaose were prepared as 100-mM stocks, whereas β-cyclodextrin was prepared as a 20-mM stock because of its lower solubility. RoCBM21 (1 mM) was titrated with individual ligands, and 2D $^{15}$N HSQC experiments were recorded to monitor the interactions. Weighted averaged $^1$H and $^{15}$N chemical shift changes were calculated using the equation $\Delta\delta_{avg}=[(\Delta\delta_{1HN})^2+(0.17\Delta\delta_{15N})^2]^{1/2}$ (Saitoh, T. et al., (2006) *J Biol Chem* 281, 10482-10488).

(D) Structural Comparison

The SBD structures for comparison are CBMs from *A. niger* glucoamylase (AnCBM20) (Sorimachi, K. et al., (1996) *J Mol Biol* 259, 970-987), *Thermoactinomyces vulgaris* R-47 α-amylase I (TvCBM34 I) (Abe, A. et al., (2004) *J Mol Biol* 335, 811-822), *Bacillus halodurans* maltohexaose-forming amylase (BhCBM25 and BhCBM26) (Boraston, A. B. et al., (2006) *J Biol Chem* 281, 587-598), and *Klebsiella pneumoniae* pullulanase (KpCBM41) (Mikami, B. et al., (2006) *J Mol Biol* 359, 690-707). Structures were superimposed using the web server "FAST" (Zhu, J., and Weng, Z. (2005) *Proteins* 58, 618-627).

(E) Docking Simulations

AutoDock3.05 (Morris, G. M. et al., (1998) *J. Computational Chemistry* 19, 1639-1662) was used to simulate the binding modes of starch molecules at the binding sites. The three-dimensional structure of cyclomaltohexaicosaose was downloaded from PDB (code: 1058). The carbohydrate molecule was docked to different binding sites in separate simulations. Affinity grids, 90×90×90, 3D-centered on the binding sites with 0.375 Å spacing were calculated using the program autogrid (Morris, G. M. et al., (1998) *J. Computational Chemistry* 19, 1639-1662). Lamarckian genetic algorithm (LGA) was used for conformational searches. For each carbohydrate at one of the two binding sites, 100 trials were made with a population size of 150 for each trial. Initial position and conformation were chosen randomly. The translation step was 2.0 Å, and the rotation step was 50°. Other docking parameters were as follows: mutation rate=0.02, crossover rate=0.8, elitism=1, local search rate=0.06, with 1 million energy evaluations. Final conformations from the 100 trials were clustered using a root mean square deviation (RMSD) tolerance of 1.5 Å.

(F) Results

NMR Spectra and Molecular Structure

The $^{15}$N HSQC of RoCBM21 showed a well-dispersed pattern of peaks characteristic of typical β-strands (FIG. 8 A). The spectral widths of proton dimensions were set to 16 ppm to accommodate the peaks. The most upfield chemical shift was −1.181 ppm, which belongs to I79 Hδ1; the Hε1 of W70 resulted in the most downfield chemical shift at 11.88 ppm. Due to the large number of aromatic residues in RoCBM21 (18/106), several chemical shifts were affected by the π-electron currents of aromatic rings. An atom that is close to an aromatic ring may experience either shielding (above or below the ring) or deshielding (in the plane of the aromatic ring) effect of the π-electron current. Some assigned chemical shifts have even been reported as anomalous or suspicious by the software currently used by BMRB to check for chemical shift outliers (Moseley, H. N. et al., (2004) *J Biomol NMR* 28, 341-355). These chemical shifts were carefully verified on request of the BMRB annotator. For example, the chemical shift of V39 Hβ (0.739) may be affected by the rings of Y83 and W47; N52 Hβ3 (0.775) by the ring of W47, N97 Hβ3 (−0.09) by the ring of Y102, I79 Hγ12 (−0.22) by the ring of Y40, and Y102 Hβ3 (0.482) by the ring of F82; as a result, their chemical shifts move upfield. In HNCA, HN(CO)CA, CBCA(CO)NH, HNCACB, HNCO, and HN(CA)CO spectra, the backbone sequential connectivity proceeds continuously through the whole protein sequence except for proline residues and glycine 18. The connectivity between Asp17, Gly18, and Ser19 is absent in all those backbone connective experiments, and thus the chemical shift of amide nitrogen from Gly18 could not be assigned unambiguously. An example view of strips demonstrating backbone connectivity in an HNCACB spectrum is shown in FIG. 8B.

The structures were calculated based on 2247 restraints as described in Experimental Procedures: 2071 NOE-derived distance constraints, 102 dihedral angle restraints, and 74 distance restraints from hydrogen bonds. NOEs of N- and C-β-sheets are illustrated in FIG. 8 C. A total of 200 structures were generated at the final iteration of the ARIA calculation. Fifteen structures with the lowest total energies were chosen for analyses and were deposited in PDB. The structure with the lowest RMSD to the average structure was chosen as the representative structure (FIG. 9 A). The NMR statistics are summarized in Table 2. The RMSD with respect to the average structure was 0.48±0.06 Å for backbone and 0.96±0.11 for heavy atoms in the well defined region, and 1.14±0.31 Å for backbone and 1.43±0.29 for heavy atoms for all residues. In the Ramachandran plot, 95% of non-glycine and non-proline residues are in the most-favored or additionally allowed region, and 98.5% are in the generously allowed region. Most of the N97 residues and several of the N45 and N101 residues of the ensemble were found in the disallowed region. N97 and N101 are located in loop 8, whereas N45 is in loop 4. These loops are in the most flexible region of RoCBM21.

TABLE 2

Structural statistics of RoCBM21 in aqueous solution at pH 4.5 and 298 K

| Experimental constraints | |
| --- | --- |
| Total | 2071 |
| Intra-residue | 973 |
| Sequential (\|I − j\| = 1) | 509 |
| Medium range (\|I − j\| <= 4) | 142 |
| Long range (\|I − j\| > 4) | 447 |
| Hydrogen bond constraints | 74 |
| Dihedral angle constraints | 102 |
| RMSD from experimental data | |
| Distance (Å) | 0.0557 ± 0.0077 |
| RMSD (Å) with respect to the average structure | |
| Well-defined region | |
| Backbone (N, C$^\alpha$, C') | 0.48 ± 0.06 |
| Heavy atoms | 0.96 ± 0.11 |
| All residues | |
| Backbone | 1.14 ± 0.31 |
| Heavy atoms | 1.43 ± 0.29 |
| Total energy Etotal after water refinement (Kcal · mol$^{−1}$) RMSD from idealized covalent geometry | −2730 ± 66 |
| Bonds (Å) | 0.0046 ± 0.0004 |
| Angles (°) | 0.546 ± 0.035 |
| Impropers (°) | 0.522 ± 0.046 |
| Ramachandran analysis | |
| Residues in most favored regions | 67.3% |
| Residues in additional allowed regions | 27.7% |
| Residues in generously allowed regions | 3.5% |
| Residues in disallowed regions | 1.5% |

Figure 8A:
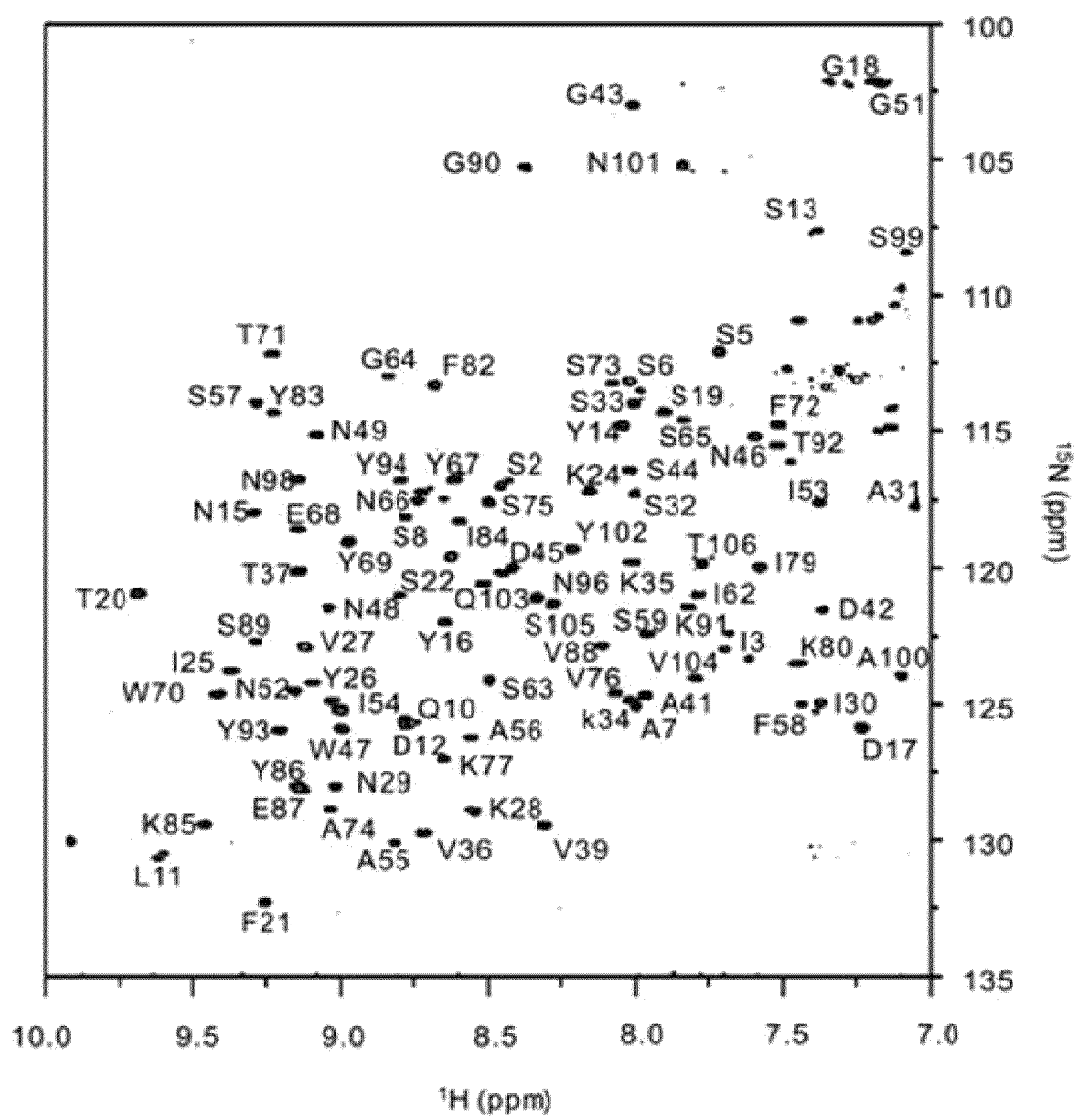
FIG. 8 shows NMR spectra of RoCBM21. A: Assignment of amide resonances of RoCBM21 on a $^1$H-$^{15}$N HSQC spectrum. All backbone amide peaks are well resolved except for Q10, which overlaps Y12, and Y86, which overlaps E87. B: Example assignment strips from residue F21 to Y26 in the HNCACB spectrum. Cα peaks are phased to the positive phase (black); Cβ, negatively phased peaks (gray). C and D: Antiparallel secondary structures with a bulged structure in the N-sheet and a loop in C-sheet. Thick arrows indicate the NOEs found between the sequential Hα and the amide proton, thick double-headed arrows indicate inter-strand Hα-Hα NOEs, thin double-headed arrows indicate inter-strand amide proton to amide proton NOEs, thin arrows indicate inter-strand Hα to amide proton NOEs, and dotted lines indicate inter-strand hydrogen bonds. NOEs in the loop regions are not shown.
Figure 8B:
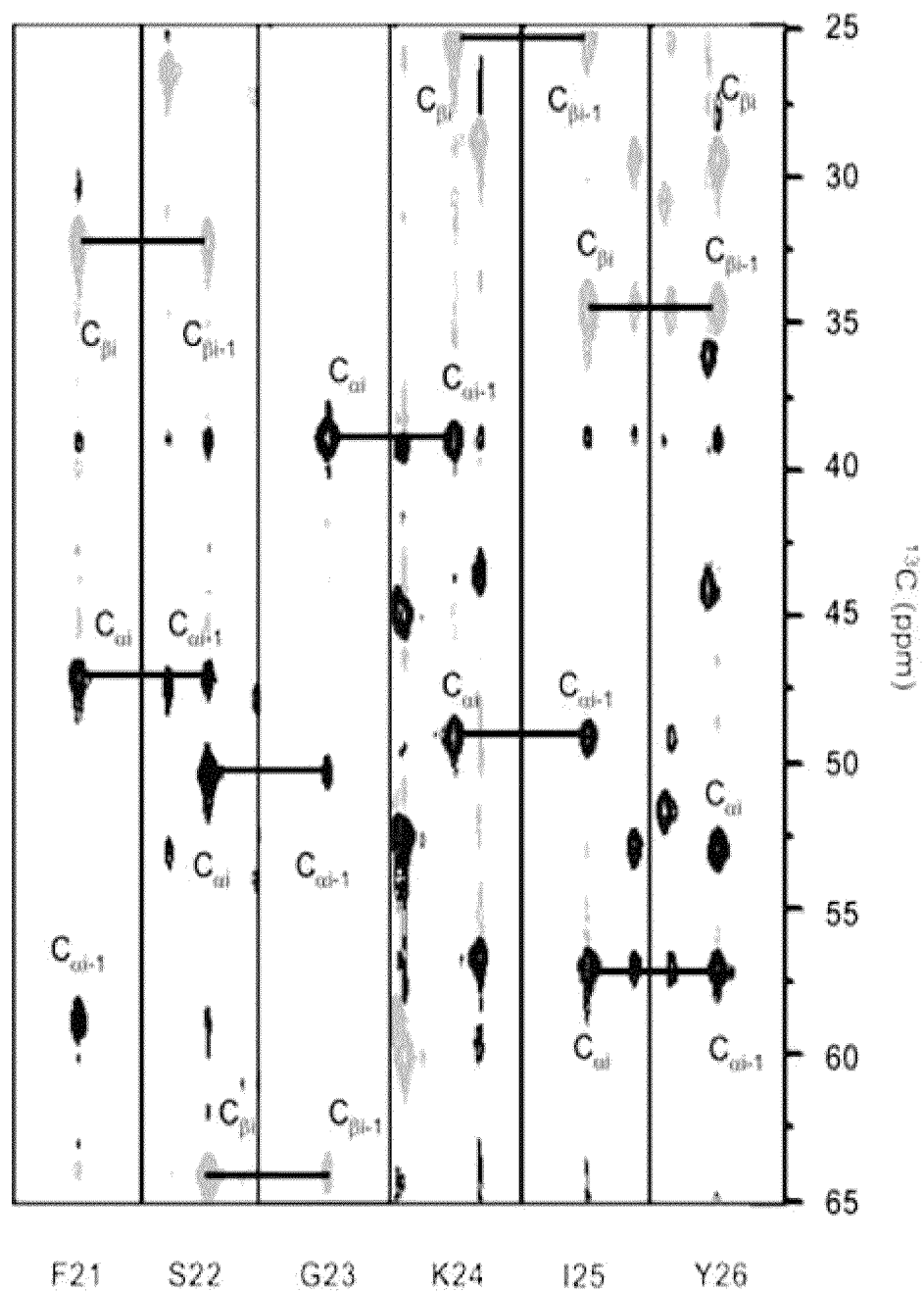
Figure 8C:
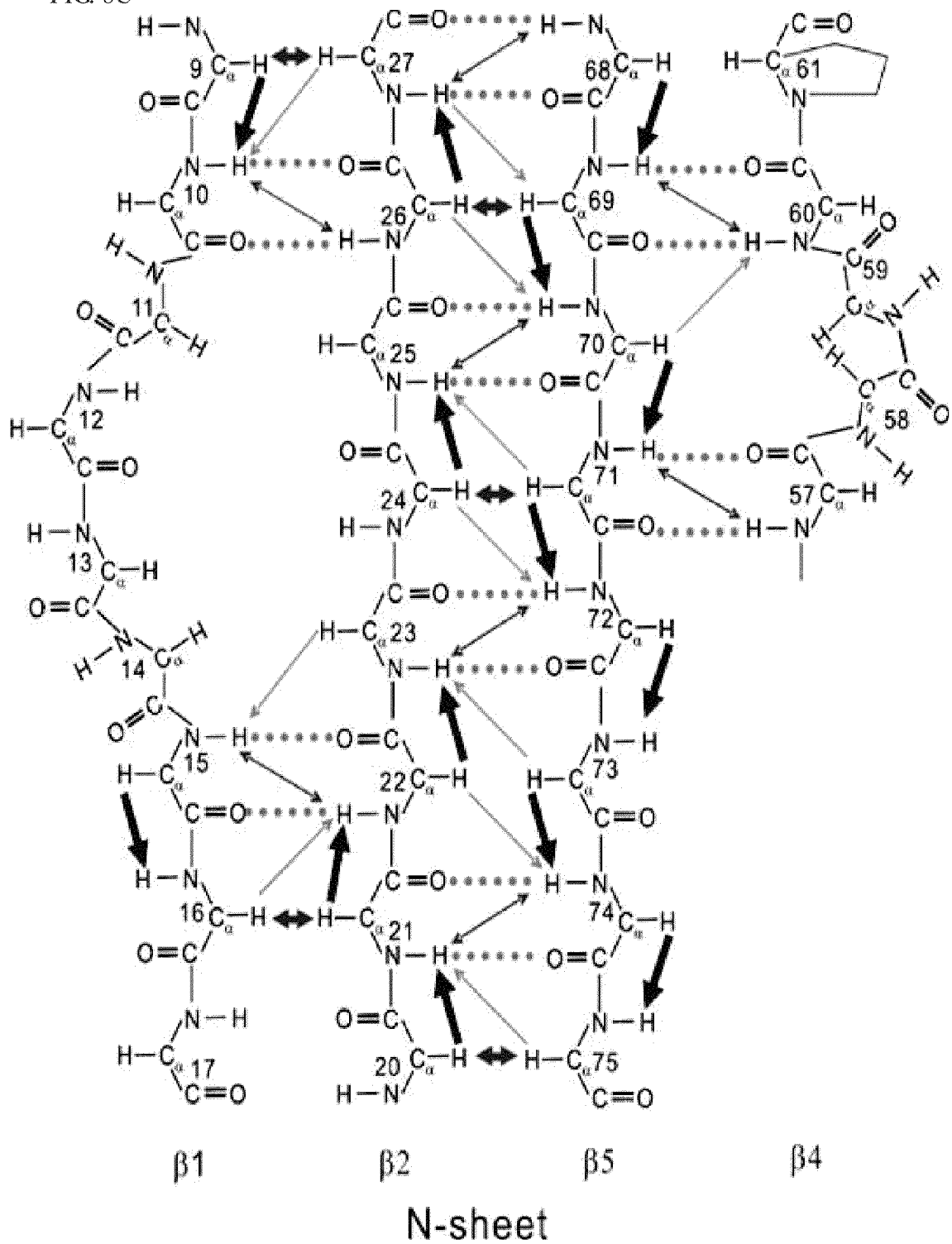
Figure 8D:
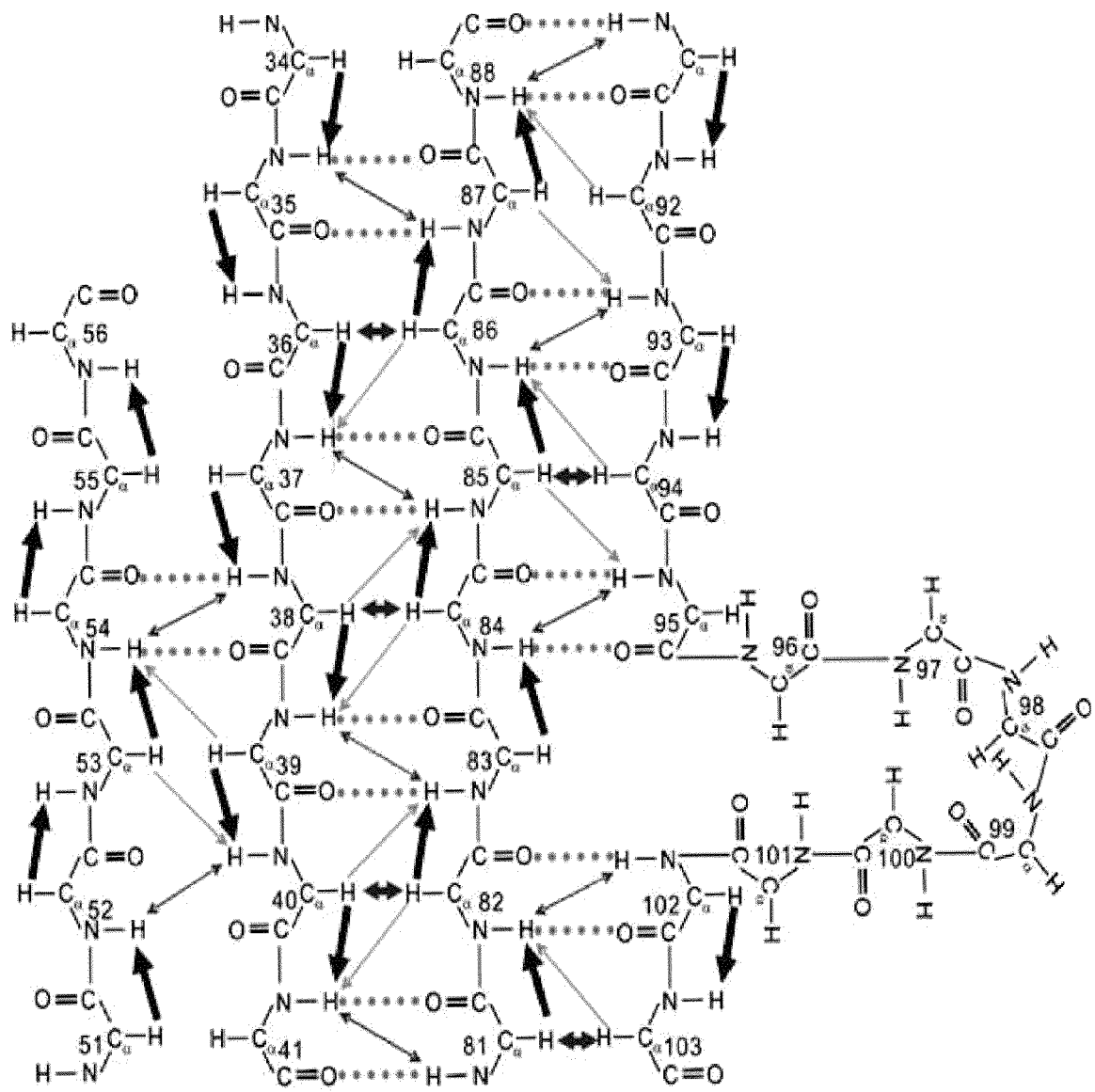
Figure 9A:
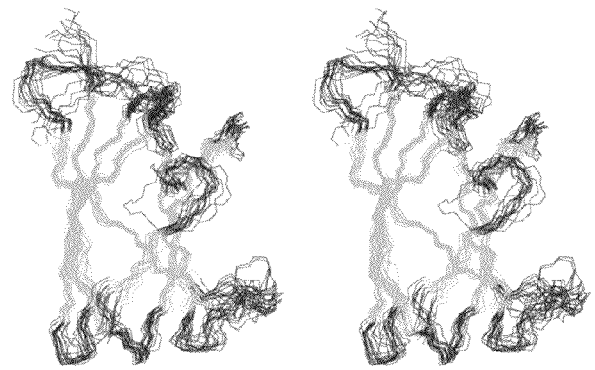
FIG. 9 shows solution structure of RoCBM21. A: Stereo view of the RoCBM21 ensemble. The front side of RoCBM21 is shown with the N-terminal loop up and C-terminal loop down. Strands are in cyan. B and C: N-sheet and C-sheet sides of the β-sandwich fold of RoCBM21. D and E: Surface view of B and C.
Figure 9B:
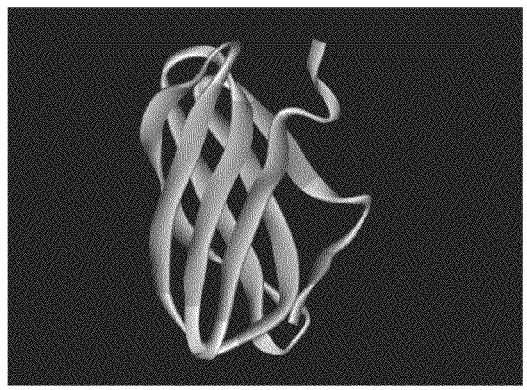
Figure 9C:
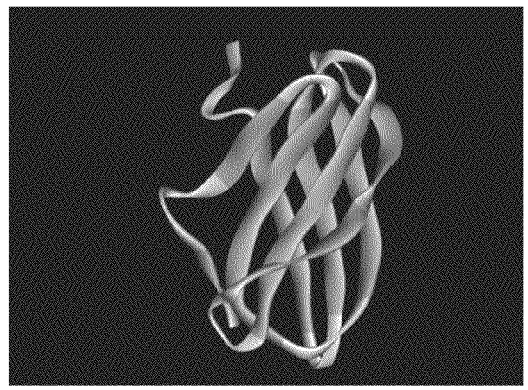
Figure 9C:
Figure 9D:
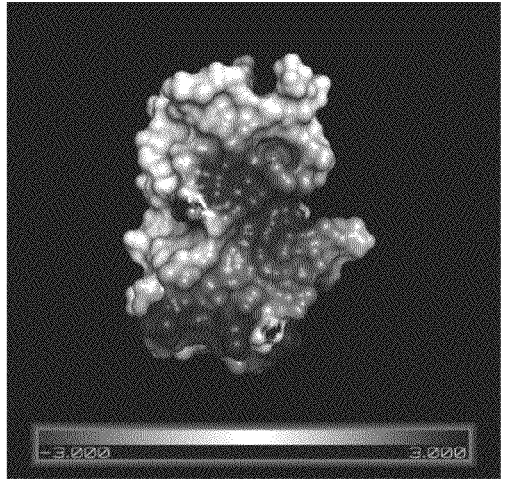
Figure 9E:
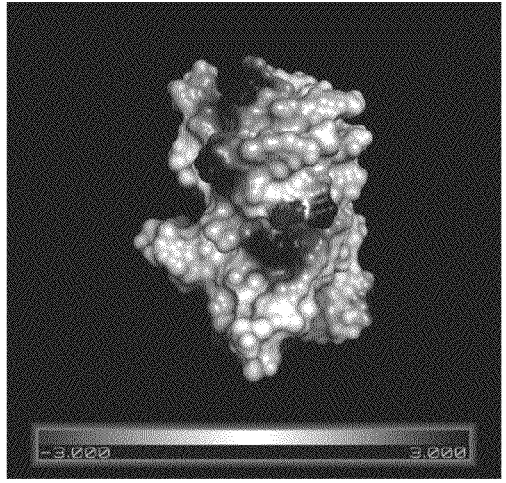

The RoCBM21 domain contains 106 residues, the sequence of which has little similarity (<25%) with other SBD families. The solution structure of RoCBM21, however, shows a conventional β-sandwich fold and an immunoglobulin-like architecture that are characteristic of most CBMs (Boraston, A. B. et al., (2004) *Biochem J* 382, 769-781). The β-sandwich is symmetric and is composed of eight antiparallel β-strands: β1 (V9-Y16), β2 (F21-V27), β3 (V34-D42), β4 (I53-G60), β5 (Y67-A74), β6 (I79-V88), β7 (T92-N95), and β8 (Y102-V104). These β-strands can be subdivided into a N-terminal strand containing β-sheet (N-sheet) (FIG. 9 B), consisting of β1β2β5, and a C-terminal strand containing β-sheet (C-sheet) (FIG. 9 C), consisting of β3β6β7/8, which are connected by β4. Strand β2, positioned in the middle of the N-sheet, is paired antiparallel to β1 and β5, whereas β6-positioned in the middle of the C-sheet is paired antiparallel to β3, β7, and β8. Strand β4, which is partially paired antiparallel to β3 and β5, lies across both β-sheets. The hydrophobic core of RoCBM21 is composed of V9, L11, I14, Y16, F21, I25, V27, W70, and F72 in the N-sheet and V36, V38, Y40, F82, I84, Y86, V88, Y93, Y102, and V104 in the C-sheet. In β1, residues L11-Y14 are not hydrogen bonded to β2, and they form a bulge (FIG. 8 C). Both β7 and β8 are hydrogen bonded to β6, and they are spanned by loop 8 (FIG. 8D). The solvent-accessible surface of the RoCBM21 structure is shown in FIGS. 9D and E. The DelPhi electrostatic potential (Rocchia, W. et al., (2001) *J. Phys. Chem. B* 105, 6507-6514) was mapped onto the surface. Interestingly, the surfaces of the N- and C-sheets show very distinct electrostatic potential distributions, with the surface of the N-sheet contains more negatively charged residues whereas that of the C-sheet contains more positively charged residues.

Structural Comparisons to SBDs

Figure 10A:
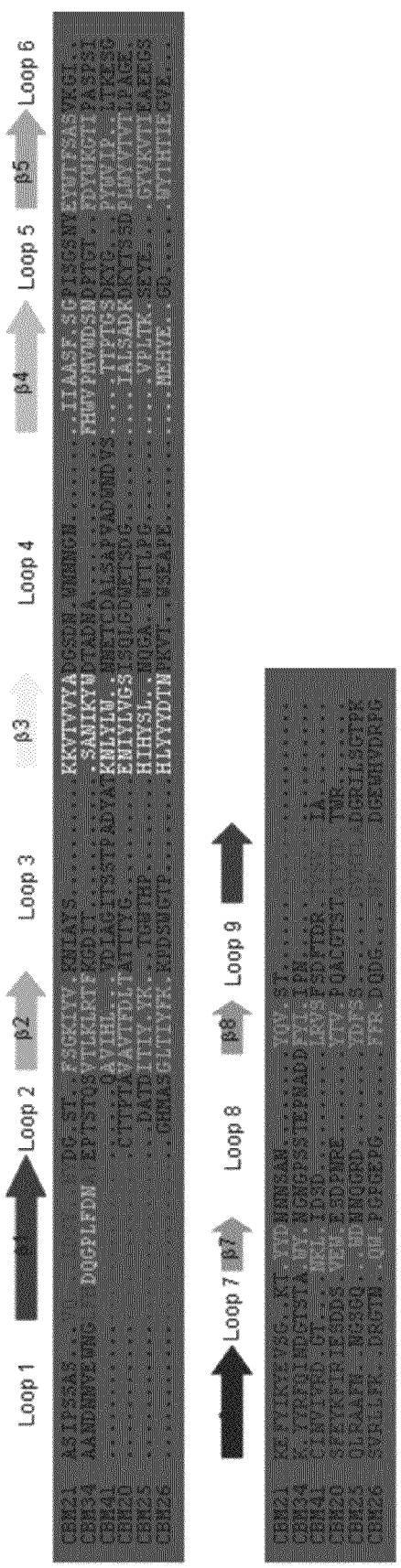
FIG. 10 shows type I topology and type II topology of SBDs. Red, orange, yellow, green, blue, indigo and violet represent the regions of the eight β-strands in RoCBM21 and their corresponding strands in other SBDs. Strands 7 and 8, both shown in violet, form hydrogen bonds with strand 6. The extra loop between the first two β-strands (corresponding to the bulged structure of RoCBM21) at the N terminus of TvCBM34 I is pink. A: Primary structures of SBDs. The sequences corresponding to secondary structure are colored as indicated above. B: Schematic diagrams of type I topology and type II topology. The strand order is equivalent to that shown in A and is shown above the type II topology diagram. C: Three-dimensional structures of type I topology (represented by AnCBM20) and type II topology (represented by RoCBM21).
Figure 10B:
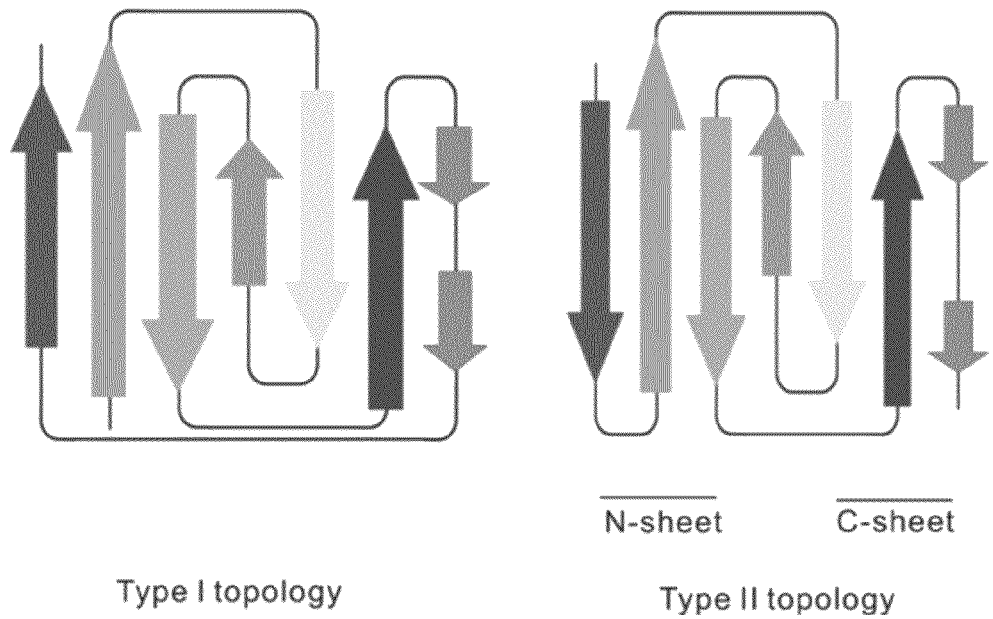
Figure 10C:
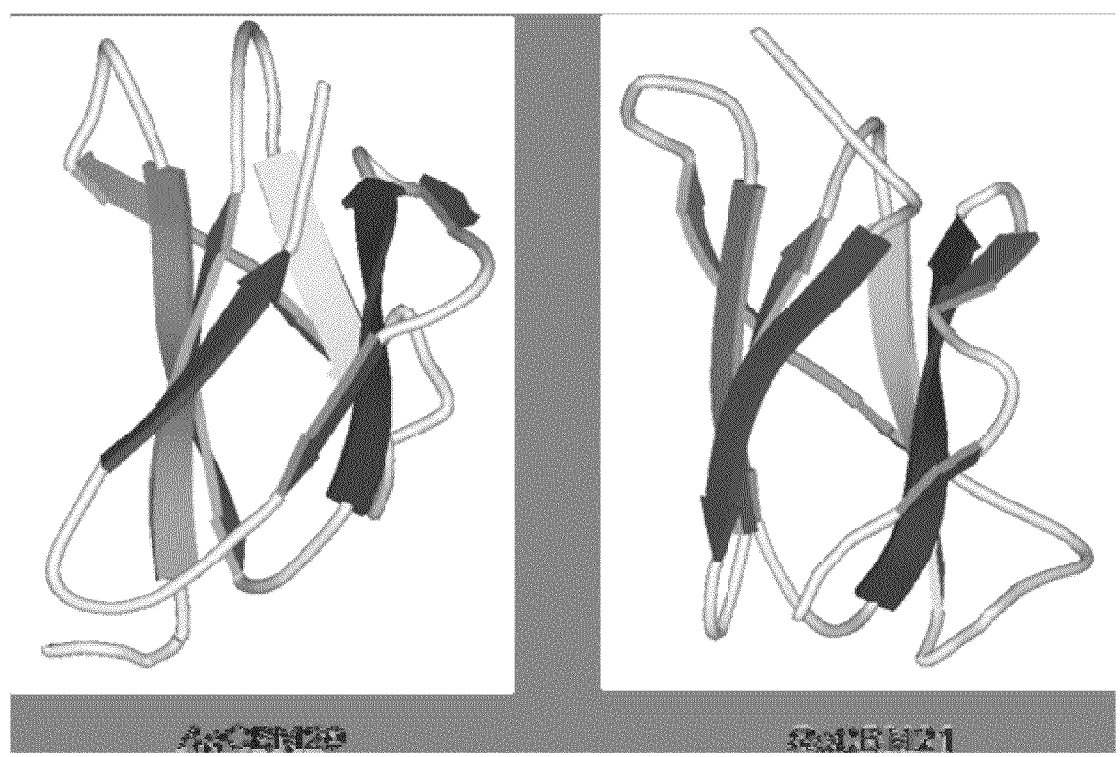

The RoCBM21 structure with those of different SBD families was compared (Table 3). FIGS. 10 A-D show the similarity in primary, secondary, and tertiary structures. Equivalent β-strands and loops in different families of SBDs are labeled and colored according to the structure of RoCBM21 (FIG. 10 A). Two types of topologies can be discerned from the structural comparison: The structures of AnCBM20, BhCBM25, BhCBM26, and KpCBM41 have type I topology, whereas the RoCBM21's and TvCBM34's structures have type II topology. These two topology types are similar except that a strand must be shifted to overlap of two topologies. For example, β1 in AnCBM20 is equivalent to β2 in RoCBM21; subsequent strand equivalents can be fitted, one by one, and the final strand (β8) of RoCBM21 is superimposable with strand 7 of AnCBM20.

Figure 11A:
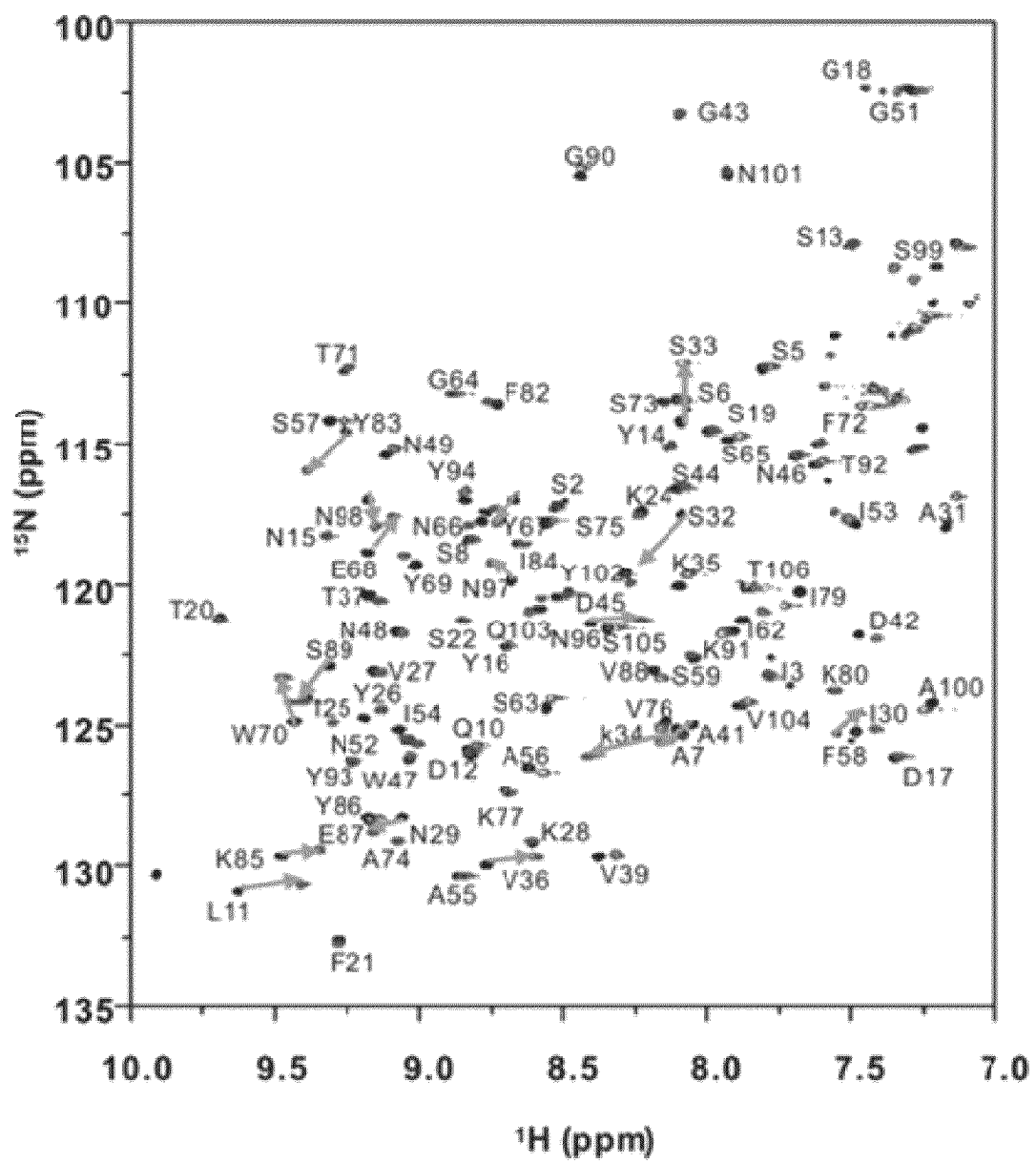
FIG. 11 shows ligand-binding and ligand-docking studies of RoCBM21. A: The RoCBM21 $^1$H-$^{15}$N HSQC spectrum before (black peaks) and after (red peaks) titration (β-cyclodextrin as ligand). Peaks with larger chemical shift perturbations are indicated with green arrows. B: Weighted averaged chemical shift changes with respect to residue number. Black, light yellow and red represent ligands: maltotriose, maltoheptaose, and β-cyclodextrin, respectively. Asterisks indicate the asparagine (N) residues in the poly-N loops with chemical shift changes >0.1. The perturbation thresholds are set to >0.1 and 0.06-0.1 (transverse plains). C: RoCBM21 structure labeled with residues that are affected upon titration. Residues with chemical shift changes >0.06 are considered as significantly affected and are colored green, and those with chemical shift changes >0.1 (and thus hypothesized to play critical roles in ligand binding) are shown as stick structures.
Figure 11B:
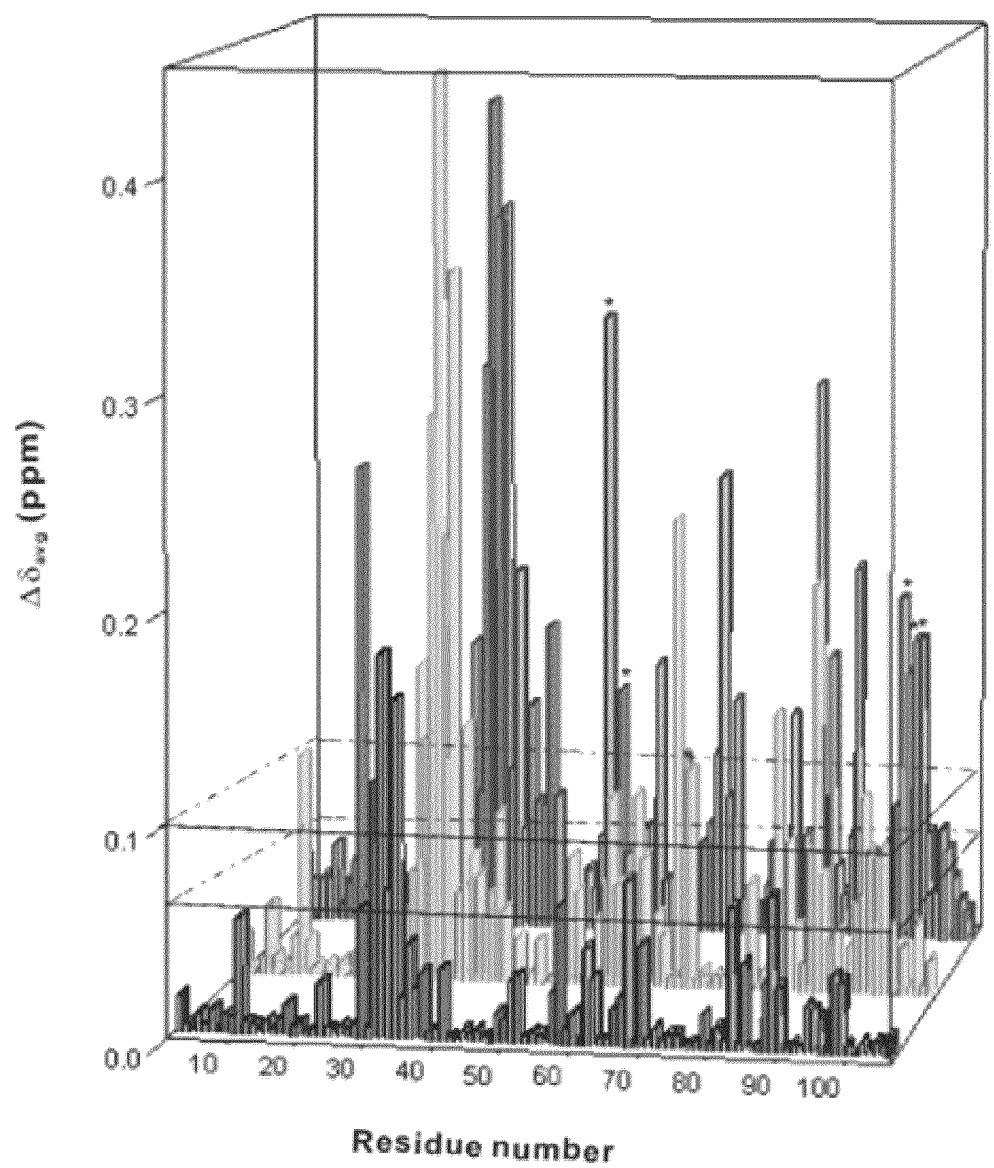
Figure 11C:
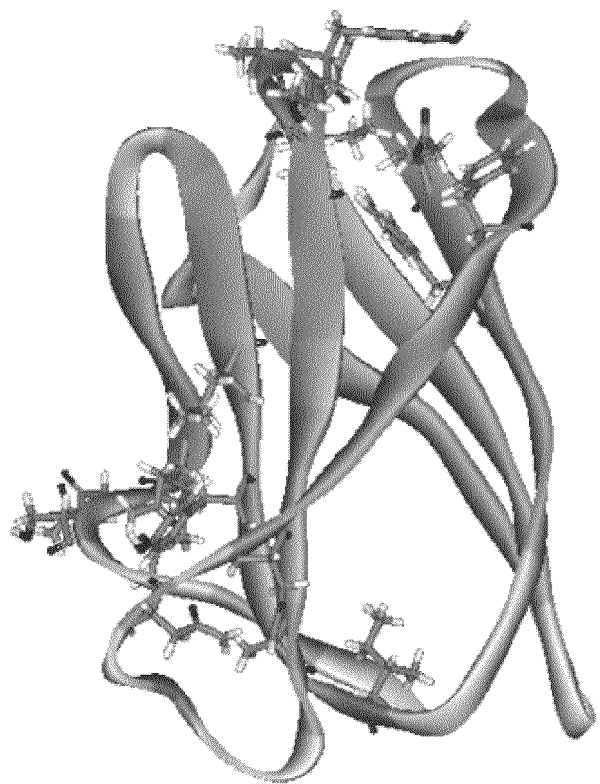
Figure 11D:
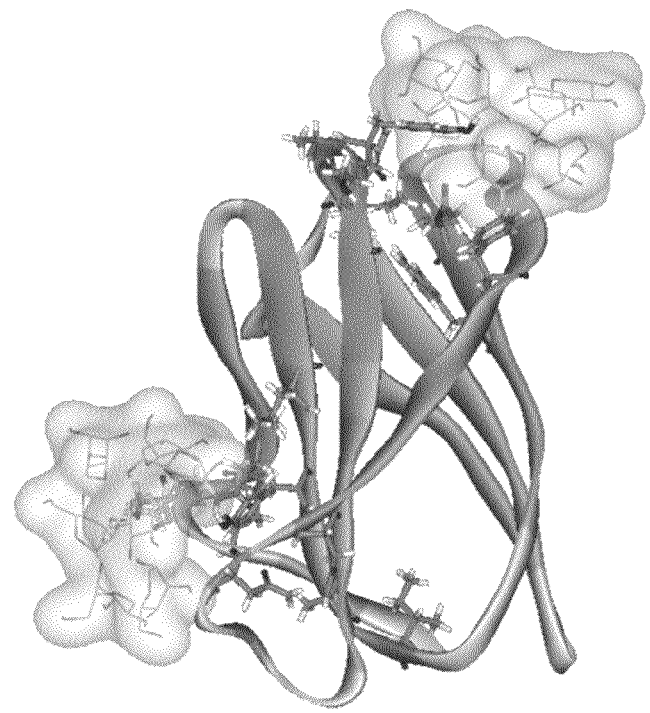

Notably, the final strand in AnCBM20 plays the role of β1 in RoCBM21, forming hydrogen bonds with the middle strand (β2 or its equivalent) of the N-terminal β-sheet. All β-strands in RoCBM21 are antiparallel, but the first and the last strands are parallel in AnCBM20. In sum, the overall topology of RoCBM21 (type II topology) is similar to that of AnCBM20 (type I topology), but the order of the equivalent strands is shifted by one. It appears that most N-terminal SBDs have type II topology whereas the C-terminal SBDs have type I topology (except for KpCBM41) (Table 3) (Mikami, B. et al., (2006) *J Mol Biol* 359, 690-707).

titration with carbohydrate ligands caused large chemical shift perturbations in asparagines N50, N52, N96, N97, and N98. These poly-N loops may act as molecular determinants of CBM-starch interactions. The presence of these poly-N loops is a distinct feature of some members of CBM21 (Machovic, M. et al., (2005) *Febs J* 272, 5497-5513). Two molecules of β-cyclodextrin are docked respectively into the site I and site II of RoCBM21 (FIG. 11D). In site 1, hydrogen bonds were also observed between the hydroxyl groups O2 and O3 of glucose residues in the docked β-cyclodextrin and the asparagine-rich loops of RoCBM21. In site II, side chains of N29 and Y32 were hydrogen-bonded with the β-cyclodextrin; this was consisted with the large chemical shift changes observed.

Figure 11E:
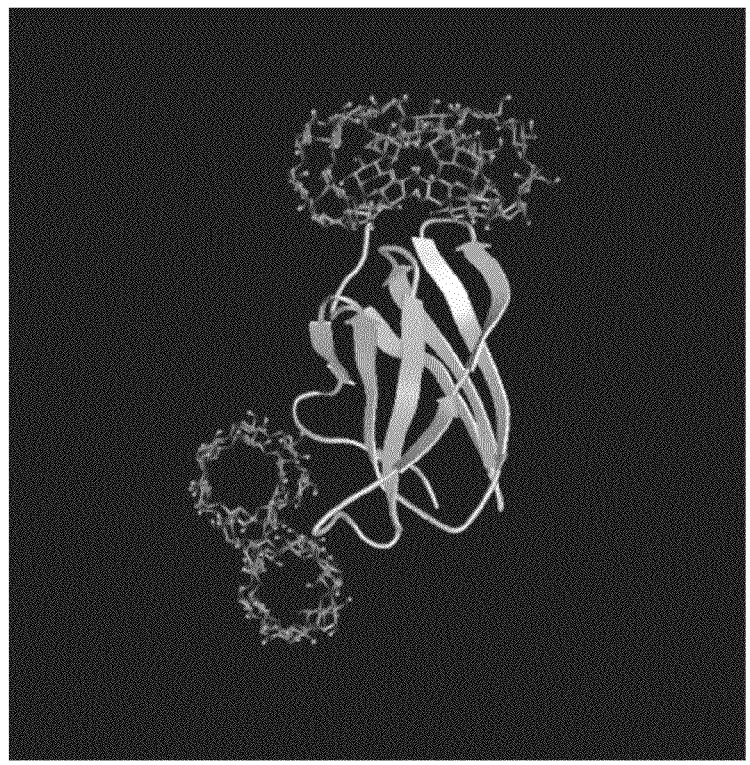
Figure 11F:
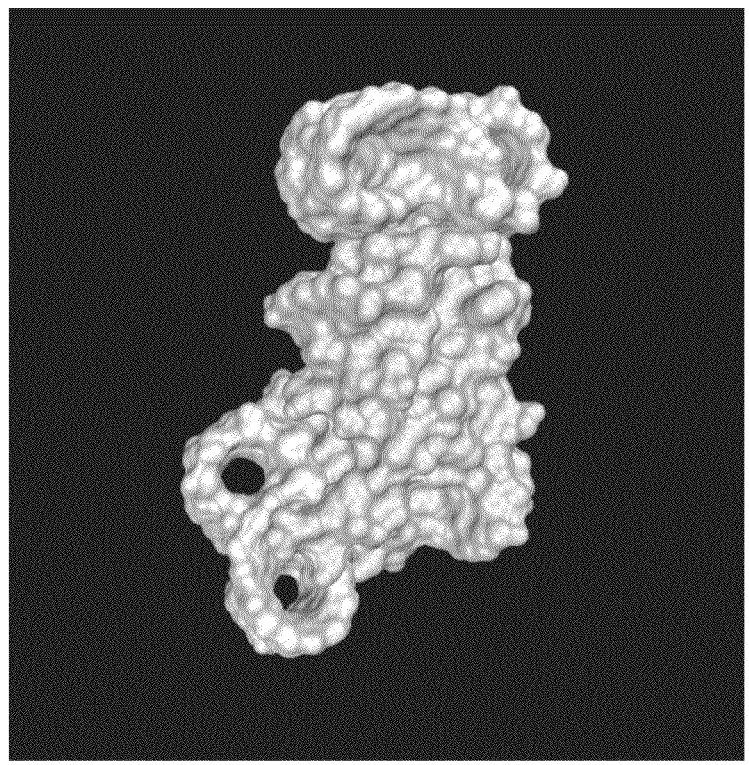

Since most ligands utilized in SBDs studies were relatively small (numbers of glucose ≤7) and did not contain intact helical structure of starch. To mimic the binding of a larger amylose molecule, a cyclomaltohexaicosaose molecule (Gessler, K. et al., (1999) *Proc Natl Acad Sci USA* 96, 4246-4251) (v-amylose, PDB code: 1C58) was docked into sites I and site II of RoCBM21 respectively (FIGS. 11E and F). In site I of the docked complex, loop 4 interacts with the v-amylose in the helical groove between G1-G13 and G14-G26, and loop 8 interacts with glucose residues in the helical groove

|  | RoCBM21 | TvCBM34 | AnCBM20 | BhCBM25 | BhCBM26 | KpCBM41 |
|---|---|---|---|---|---|---|
| Module arrangement (N- or C-terminal) | N | N | C | C | C | N |
| PDB code | 2DJM | 1UH3 | 1KUL | 2C3X | 2C3G | 2FHF |
| Sequence range (By PDB numbering) | 1-106 | 1-123 | 509-616 | 10-102 | 1-98 | 53-155 |
| Sequence identity (%) | 100 | 10.6 | 7.9 | 13.2 | 8.3 | 6.3 |
| Sequence similarity (%) | 100 | 21.6 | 16.7 | 20.8 | 20.0 | 1.4 |
| RMSD to RoCBM21 (Å) | 0 | 2.8 | 2.6 | 3.6 | 2.8 | 3.5 |
| Topology type | II | II | I | I | I | I |

The sequence range in pdb files of BhCBM25 and BhCBM26 are corresponding to amino acids 863-958 and 771-863 of open reading flame BH0413.

Ligand-Binding and Chemical Shift Perturbation

Three linearly linked carbohydrates (maltotriose, maltoheptaose, and β-cyclodextrin) tested in this study showed similar patterns of chemical shift perturbation; the same amino acid residues were affected in the titrations, but the magnitude of the change differed between carbohydrates. The $^{15}$N HSQC spectra of RoCBM21 before and after titration with β-cyclodextrin overlapped (FIG. 11A), and a summary of the chemical shift changes and the residues affected is plotted in FIG. 11B. The RoCBM21 residues that exhibited significant chemical shift perturbations (>0.1 ppm and 0.06-0.1 ppm) were mapped on the three-dimensional structure (FIG. 11C). According to these perturbations, the residues affected by ligand-binding can be cataloged into three types. First, residues A41, W47, N52, Y83, K85, K91, D95, N96, N97, and S99 are located at the corresponding site I of previously reported SBDs. Likewise, residues N29, I30, A31, Y32, S33, K34, S57, F58, I62, N66, Y67, E68, and Y69 form the corresponding site II. The residues with significant chemical shift changes and two carbohydrate-binding sites were mapped on the structure of RoCBM21 (FIG. 11C). Interestingly, several residues located in the hydrophobic core were also affected by ligand-binding; they are L11, V36, V38, W70, and I79. Loops 1, 4, and 8 are flexible regions with average RMSD values >1.5 Å. Besides high flexibility, loops 4 and 8, which enclose site I, share another feature—they are rich in asparagine residues (N46, N48, N49, N50, and N52 are in loop 4, and N96, N97, N98, and N101 in loop 8). The between G2-G4 and G8-G10. In site II, loop 3 inserts into the helical groove between G1-G13 and G14-G26, and N29 and Y32 interact with glucose residues. Loop 5 binds the v-amylose structure at the edge rather than in the groove.

Example 4

(A) Materials and Methods

The concentration of the RoGACBM21 used in crystallization was approximately 10 mg/mL The RoGACBM21-β-cyclodextrin (βCD) complex crystals were grown at a molar ratio of 1:2. Crystallization trails were carried out by the hanging-drop vapor-diffusion method. 1 μl protein solution was mixed with 1 μl reservoir solution and equilibrated against a 500 μl reservoir solution in Linbro plates. Initial crystallization conditions were obtained using Hampton Research Crystal Screen kits and then further optimized to obtain diffraction quality crystals. The X-ray diffraction data of RoGACBM21-βCD complex crystal was collected on BL13C1 using wavelength 0.9762 Å, at NSRRC in Taiwan. Crystals were mounted in a nylon loop and flash-frozen in a liquid-nitrogen stream at 100 K. The data were processed and scaled using the program HKL2000.

(B) Results

The RoGACBM21-βCD complex crystals (FIG. 12) grew to maximum dimensions of 0.2×0.2×0.5 mm within 4 days at 293 K using 18% PEG 8000 and 0.2 M zinc acetate in 0.1 M Na Cacodylate buffer (pH 6.5). The RoGACBM21-βCD complex crystal diffracted to 1.8 Å and belong to the orthorhombic $P2_12_12_1$ space group with unit-cell parameters a=42.58 Å, b=42.71 Å, c=70.06 Å, α=β=γ=90° and an $R_{merge}$ of 3.4%. The $V_M$ (Matthews 1968) was calculated to be 2.73 $Å^3Da^{-1}$, corresponding to a solvent content of 55%, containing one molecule per asymmetric unit in the crystal. In the RoGACBM21-βCD complex (FIG. 13), one RoGACBM21 molecule binds with one β-cyclodextrin molecule. Two binding sites, site I and site II, were observed in the RoGACBM21-βCD complex. Site I is located around loop β2-β3 containing a key Y32 residue and site II is located around loop β3-β4 with another polysaccharide recognition residue W47.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, plants, microorganisms, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for identifying starch binding sites of starch binding domain in CBM family, comprising:
   (a) obtaining structure of objective starch binding domain by NMR spectroscopy;
   (b) simulating binding mode of objective starch binding domain between affected residues from chemical shift perturbation of the structure of objective starch binding domain and an oligosaccharide via a docking tool to present predicted binding residues;
   (c) obtaining crystal structure of a complex of objective starch binding domain and the oligosaccharide via X-ray crystallography to present ligand-binding residues; and
   (d) selecting matched residues from the predicted binding residues and the ligand-binding residues to identify the starch binding sites of starch binding domain;
   wherein the CBM family is consisting of CBM20, CBM21, CBM25, CBM26, CBM34, or CBM41.

2. The method of claim 1, wherein the CBM family is CBM20 or CBM21.

3. The method of claim 2, wherein the CBM family is CBM21.

4. The method of claim 1, wherein the oligosaccharide is maltotriose, maltoheptaose, or β-cyclodextrin.

5. The method of claim 1, wherein the starch binding sites of starch binding domain are aromatic amino acids.

6. The method of claim 5, wherein the starch binding sites of starch binding domain are tyrosine, tryptophan, or phenylalanine.

7. The method of claim 1, wherein the identified starch binding sites of starch binding domain in CBM21 are residues 32, 47, 58, 67, 83, 93, or 94 in SEQ ID NOs. 1, 2, and 3.

8. The method of claim 1, further comprising obtaining protein topology of objective starch binding domain before step (a).

9. The method of claim 1, further comprising predicting starch binding sites of starch binding domain in CBM family using the identified starch binding sites of starch binding domain with same topology.

* * * * *

SEQUENCE LISTING

```
<160> NUMBER OF SEQ ID NOS: 20

<210> SEQ ID NO 1
<211> LENGTH: 107
<212> TYPE: PRT
<213> ORGANISM: Rhizopus spp.
<220> FEATURE:
<221> NAME/KEY: BINDING
<222> LOCATION: (1)..(107)

<400> SEQUENCE: 1

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105

<210> SEQ ID NO 2
<211> LENGTH: 107
<212> TYPE: PRT
<213> ORGANISM: Rhizopus spp.
<220> FEATURE:
<221> NAME/KEY: BINDING
<222> LOCATION: (1)..(107)

<400> SEQUENCE: 2

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asp Gly Ser Asp Asn Trp Asn
        35                  40                  45

Asn Asn Gly Asn Thr Ile Ala Ala Ser Tyr Ser Ala Pro Ile Ser Gly
    50                  55                  60

Ser Asn Tyr Glu Tyr Trp Thr Phe Ser Ala Ser Ile Asn Gly Ile Lys
```

```
                    65                  70                  75                  80
Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105

<210> SEQ ID NO 3
<211> LENGTH: 107
<212> TYPE: PRT
<213> ORGANISM: Rhizopus spp.
<220> FEATURE:
<221> NAME/KEY: BINDING
<222> LOCATION: (1)..(107)

<400> SEQUENCE: 3

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asn Gly Ser Asp Asn Trp Asn
        35                  40                  45

Asn Asn Gly Asn Thr Ile Ala Ala Ser Tyr Ser Ala Pro Ile Ser Gly
    50                  55                  60

Ser Asn Tyr Glu Tyr Trp Thr Phe Ser Ala Ser Ile Asn Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105

<210> SEQ ID NO 4
<211> LENGTH: 28
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(28)

<400> SEQUENCE: 4
tcccaagctt tccaagccca ctactact                                  28

<210> SEQ ID NO 5
<211> LENGTH: 28
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(28)

<400> SEQUENCE: 5
acggggtacc gttaccagtt gggaatga                                  28

<210> SEQ ID NO 6
<211> LENGTH: 30
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(30)
```

<400> SEQUENCE: 6
cccaagctta ctagtggttc tggtcatcac                                      30

<210> SEQ ID NO 7
<211> LENGTH: 28
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(28)

<400> SEQUENCE: 7
aacatatgca tggttgagga gaagcccg                                        28

<210> SEQ ID NO 8
<211> LENGTH: 27
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(27)

<400> SEQUENCE: 8
ttcggggtac cgcaagtatt cctagca                                         27

<210> SEQ ID NO 9
<211> LENGTH: 27
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(27)

<400> SEQUENCE: 9
gggaattcca tatggcaagt attccta                                         27

<210> SEQ ID NO 10
<211> LENGTH: 26
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(26)

<400> SEQUENCE: 10
tccgctcgag tcatgtagat acttgg                                          26

<210> SEQ ID NO 11
<211> LENGTH: 60
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(60)

<400> SEQUENCE: 11
tgcgcccaag cttaagaaga agaagaagaa gaagaaggca agtattccta gcagtgcttc     60

```
<210> SEQ ID NO 12
<211> LENGTH: 58
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(58)

<400> SEQUENCE: 12
ccggggtacc cttcttcttc ttcttcttct tcttctttct agatacttgg taattggc         58

<210> SEQ ID NO 13
<211> LENGTH: 50
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(50)

<400> SEQUENCE: 13
tcccaagctt caccaccacc accaccacgc aagtattcct agcagtgctt                   50

<210> SEQ ID NO 14
<211> LENGTH: 49
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(49)

<400> SEQUENCE: 14
acggggtacc gtggtggtgg tggtggtgtg tagatacttg gtaattggc                    49

<210> SEQ ID NO 15
<211> LENGTH: 60
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(60)

<400> SEQUENCE: 15
tcccaagctt actccgactc cgactccgac tccgactgca agtattccta gcagtgcttc        60

<210> SEQ ID NO 16
<211> LENGTH: 58
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(58)

<400> SEQUENCE: 16
tcggggtacc agtcggagtc ggagtcggag tcggagttgt agatacttgg taattggc          58

<210> SEQ ID NO 17
<211> LENGTH: 27
<212> TYPE: DNA
<213> ORGANISM: Artificial Sequence
```

```
<220> FEATURE:
<223> OTHER INFORMATION: designed primer
<220> FEATURE:
<221> NAME/KEY: primer_bind
<222> LOCATION: (1)..(27)

<400> SEQUENCE: 17
tttcggggta cccagagtga gccggag                                          27

<210> SEQ ID NO 18
<211> LENGTH: 22
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(22)

<400> SEQUENCE: 18
ggaattcatg gtgagcaagg gc                                               22

<210> SEQ ID NO 19
<211> LENGTH: 38
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(38)

<400> SEQUENCE: 19
tatcggggta ccatggtgag caagggcgag gagctgtt                              38

<210> SEQ ID NO 20
<211> LENGTH: 24
<212> TYPE: DNA
<213> ORGANISM: Artificial Sequence
<220> FEATURE:
<223> OTHER INFORMATION: designed primer
<220> FEATURE:
<221> NAME/KEY: primer_bind
<222> LOCATION: (1)..(24)

<400> SEQUENCE: 20
cccaagcttc ttgtacagct cgtc                                             24
```